US006965016B2

(12) United States Patent  (10) Patent No.: US 6,965,016 B2
Klinefelter  (45) Date of Patent: Nov. 15, 2005

(54) METHOD FOR EVALUATING AND AFFECTING MALE FERTILITY

(75) Inventor: Gary Klinefelter, Research Triangle Park, NC (US)

(73) Assignee: The United States of America as represented by the U.S. Environmental Protection Agency, Washington, DC (US)

( * ) Notice: Subject to any disclaimer, the term of this patent is extended or adjusted under 35 U.S.C. 154(b) by 34 days.

(21) Appl. No.: 09/752,514

(22) Filed: Jan. 3, 2001

(65) Prior Publication Data

US 2002/0052011 A1 May 2, 2002

Related U.S. Application Data

(63) Continuation-in-part of application No. 09/123,492, filed on Jul. 28, 1998, now Pat. No. 6,197,940, and a continuation-in-part of application No. PCT/US97/01725, filed on Jan. 29, 1997, which is a continuation-in-part of application No. 08/593,677, filed on Jan. 29, 1996, now abandoned.

(60) Provisional application No. 60/082,753, filed on Apr. 23, 1998.

(51) Int. Cl.⁷ .............................................. C07K 16/00
(52) U.S. Cl. ............................ 530/387.9; 530/388.22; 530/388.85
(58) Field of Search ......................... 530/387.9, 388.22

(56) References Cited

FOREIGN PATENT DOCUMENTS

WO      WO 9727218       7/1997

OTHER PUBLICATIONS

Naga Kubo et al. Biochem & Biophys Res. Comm. vol. 231—pp. 509–513, 1997.*
Brooks, D.E., "Characterization of a 22kDa Protein with Widespread Tissue Distribution but Which is Uniquely Present in Secretions of the Testis and Epididymis and on the Surface of Spermalozoa," *Biochimia et Biophycica Acta* 841:59–70 (1985).

Colman, *Res. in Immunology* 145:33–36 (1994).

Klinefelter, G.R., et al., "Discriminant Analysis Indicates a Single Sperm Protein (SP22) is Predictive of Fertility Following Exposure to Epididymal Toxicants," *Journal of Andrology* 18(2):139–150 (1997).

Primakoff, *American Journal of Reproductive Immunology*, 31:208–210 (1994).

Wagenfeld, A. et al., "Molecular Cloning and Expression of Rat Contraception Associated Protein 1 (CAP1), a Protein Putatively Involved in Fertilization," *Biochemical and Biophysical Research Communications* 251:545–549 (1998).

Welch, J.E., et al., "SP22: A Novel Fertility Protein from a Highly Conserved Gene Family," *Journal of Andrology* 19(4):385–393 (1998).

Welsch, J.E., "A 22kDa Sperm Protein (SP22) Correlated with Rat Fertility Exhibits Homology with the J–1/thiJ Family of Proteins," *Molecular Biology of the Cell* 8:325a (1997).

Yee, et al., *Contraceptive Vaccines with Sperm Proteins* 693–712 (1995).

* cited by examiner

*Primary Examiner*—Patrick J. Nolan
(74) *Attorney, Agent, or Firm*—Foley Hoag, LLP

(57) ABSTRACT

A 22 kD sperm protein, SP22, correlates with fertility and predicts fertility in males. The protein can be assayed to detect decreases in fertility resulting from exposure to toxicants and pollutants which are known or suspected to decrease fertility. In an antibody is generated to this protein, the antibody recognition by sperm in an epididymal sperm sample or ejaculate would reflect the fertility of the sample. This antibody can be used as a contraceptive to inactivate sperm, screen for toxicity, select animals for artificial insemination, and select men for assisted reproductive technologies. The protein itself can be inactivated by gene knockout, which is another approach to contraception, or the protein can be added to sperm from infertile men to make fertility techniques more feasible.

5 Claims, 20 Drawing Sheets

FIG. 1

```
SP22        MASKRALVILAKGAEEMETVIPVDIMRRAGIKVTVAGLAG
      1     |||||||||||||||||||||||||||:|||||||||||    40
DJ-1        MASKRALVILAKGAEEMETVIPVDVMRRAGIKVTVAGLAG
                                           Peptide 1

SP22        KDPVQCSRDVVICPDTSLEEAKTQGPYDVVVLPGGNLGAQ
      41    ||||||||||||||||:|||:||:|||||||||||||||    80
DJ-1        KDPVQCSRDVVICPDASLEDAKKEGPYDVVVLPGGNLGAQ

SP22        NLSESALVKEILKEQENRKGLIAAICAGPTALLAHEVGFG
      81    ||||||:||||||||||||||||||||||||||||:||    120
DJ-1        NLSESAAVKEILKEQENRKGLIAAICAGPTALLAHEIGCG
                    Peptide 2

SP22        CKVTSHPLAKDKMMNGSHYSYSESRVEKDGLILTSRGPGT
      121   :|||:||||||||| ||:|||  |||||||||||||||    160
DJ-1        SKVTTHPLAKDKMMNGGHYTYSENRVEKDGLILTSRGPGT
                Peptide 3                  Peptide 4

SP22        SFEFALAIVEALSGKDMANQVKAPLVLKD
      161   |||||||||| ||::| |||||||||||            189
DJ-1        SFEFALAIVEALNGKEVAAQVKAPLVLKD
```

FIG. 2

```
1    A gctgtgcagagccgtctggcagggttgacctcctaaagggatattccatctttattaatcattag 65

66   A tagtgtggtcagagacttagcaccattggtctccccaacctggtccagacatttcagcagttta 130

131  A tcggaacagcaacaacagcaacaaaaccttcaaaatttacaagtctttaagaaatagaaATGgca 195
     B              tggcttcgcgtgggtggaggaggcgcggctgcaggtctttaagaaatagaaATGgca
     C                     ttgaacctATGttgcactgtggagttctccacttacacagcctatttatggca
1                       M   L   H   C   G   V   L   H   L   S   L   F   M   A   15

196  tccaaaagagctctggtcatcctagccaaaggagcagaggagatggagacagtgattcctgtgga 260
16     S   K   R   A   L   V   I   L   A   K   G   A   E   E   M   E   T   V   I   P   V   D 37

261  catcatgcggcgagctgggattaaagtcaccgttgcaggcttggctgggaaggaccccgtgcagt 325
38     I   M   R   R   A   G   I   K   V   T   V   A   G   L   A   G   K   D   P   V   Q   58
                                        Peptide 1

326  gtagccgtgatgtagtgatttgtccggataccagtctggaagaagcaaaaacacagggaccatac 390
59     C   S   R   D   V   V   I   C   P   D   T   S   L   E   E   A   K   T   Q   G   P   Y 80

391  gatgtggttgttcttccaggaggaaatctgggtgcacagaacttatctgagtcggctttggtgaa 455
81     D   V   V   V   L   P   G   G   N   L   G   A   Q   N   L   S   E   S   A   L   V   K 102

456  ggagatcctcaaggagcaggagaacaggaagggcctcatagctgccatctgtgcgggtcctacgg 520
103    E   I   L   K   E   Q   E   N   R   K   G   L   I   A   A   I   C   A   G   P   T   123
          Peptide 2
                                                    *
521  ccctgctggctcacgaagtaggctttggatgcaaggttacatcgcacccattggctaaggacaaa 585
124    A   L   L   A   H   E   V   G   F   G   C   K   V   T   S   H   P   L   A   K   D   K 145
                                                    Peptide 3

586  atgatgaacggcagtcactacagctactcagagagccgtgtggagaaggacggcctcatcctcac 650
146    M   M   N   G   S   H   Y   S   Y   S   E   S   R   V   E   K   D   G   L   I   L   T 167
                                                              Peptide 4

651  cagccgtgggcctgggaccagcttcgagtttgcgctggccattgtggaggcactcagtggcaagg 715
168    S   R   G   P   G   T   S   F   E   F   A   L   A   I   V   E   A   L   S   G   K   188

716  acatggctaaccaagtgaaggccccgcttgttctcaaagacTAGagagcccaagccctggaccct 780
189    D   M   A   N   Q   V   K   A   P   L   V   L   K   D   *                      202

781  ggaccccaggctgagcaggcattggaagcccactagagagaccacagcccagtgaacctggcat 845

846  tggaagcccactagtgtgtccacagcccagtgaacctcaggaactaacgtgtgaagtagcccgct 910

911  gctcaggaatctcgccctggctctgtactattctgagccttgctagtagaataaacagttcccca 975

976  agctc*c*tgacggct*                                                         989
```

FIG. 6
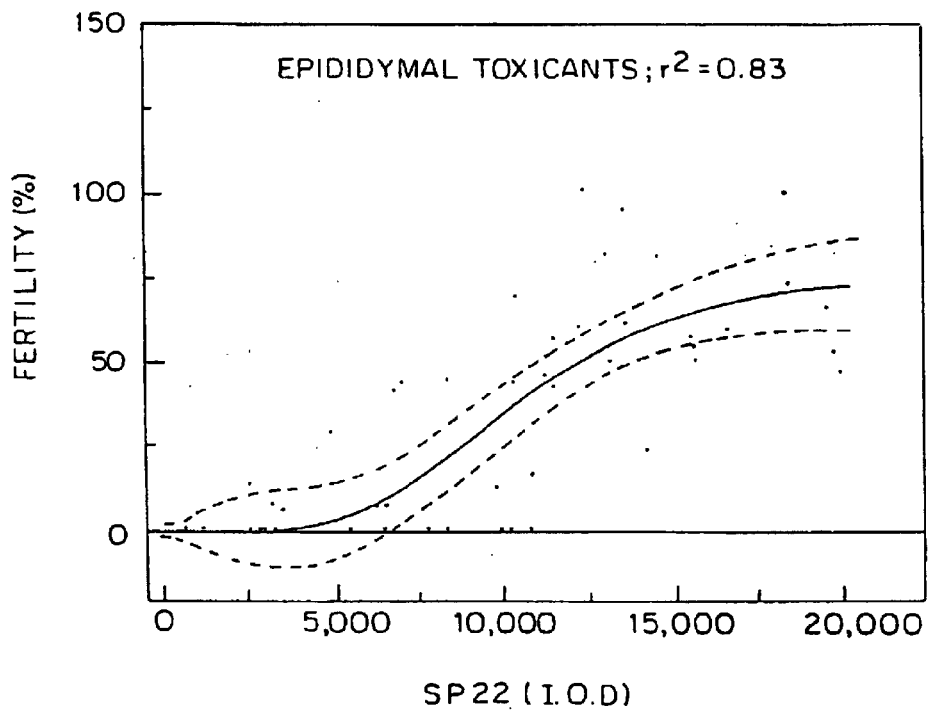
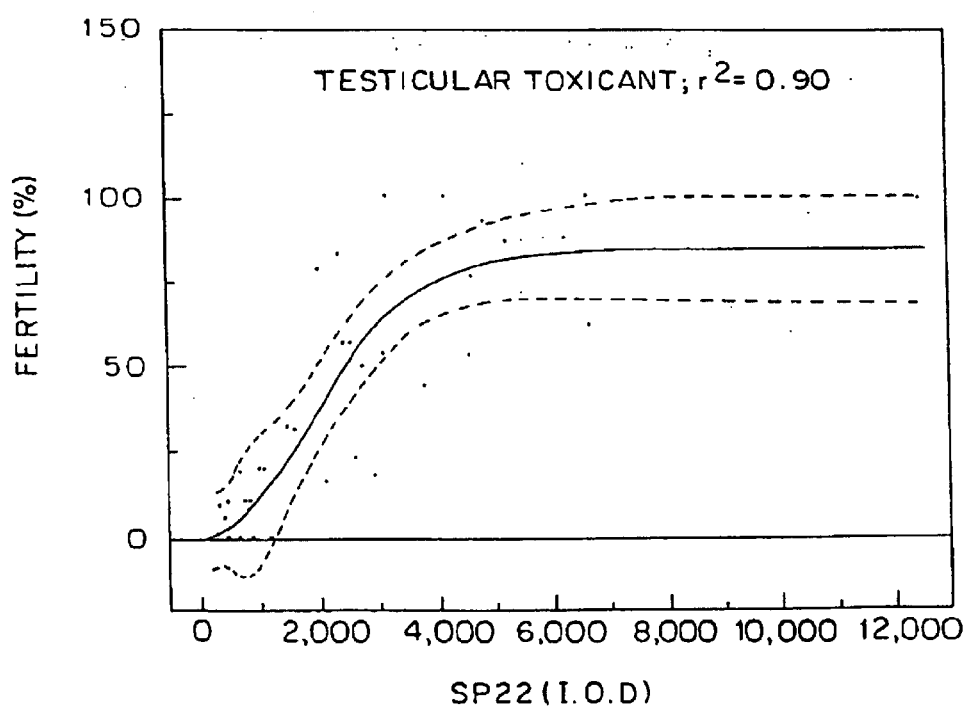

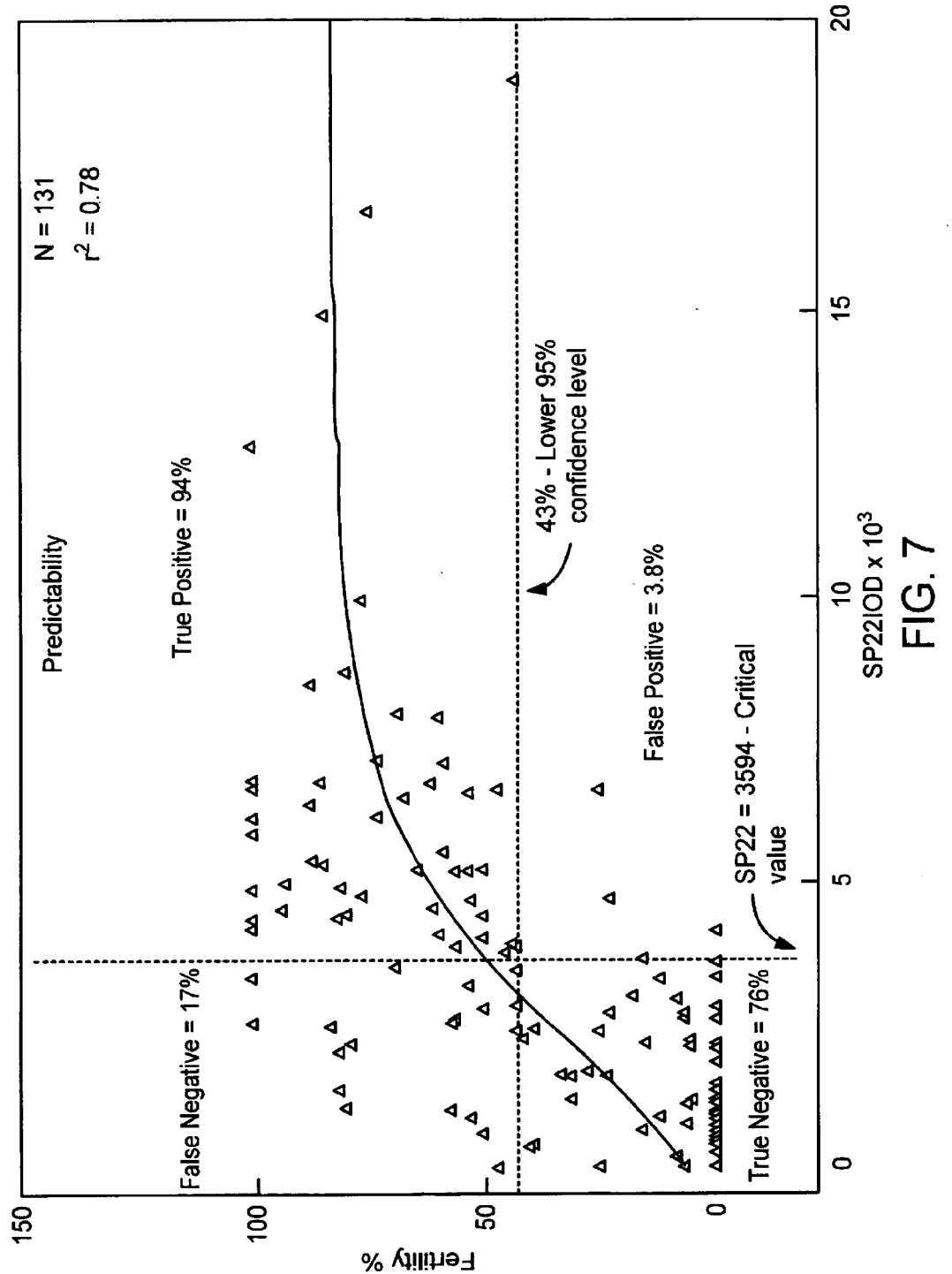

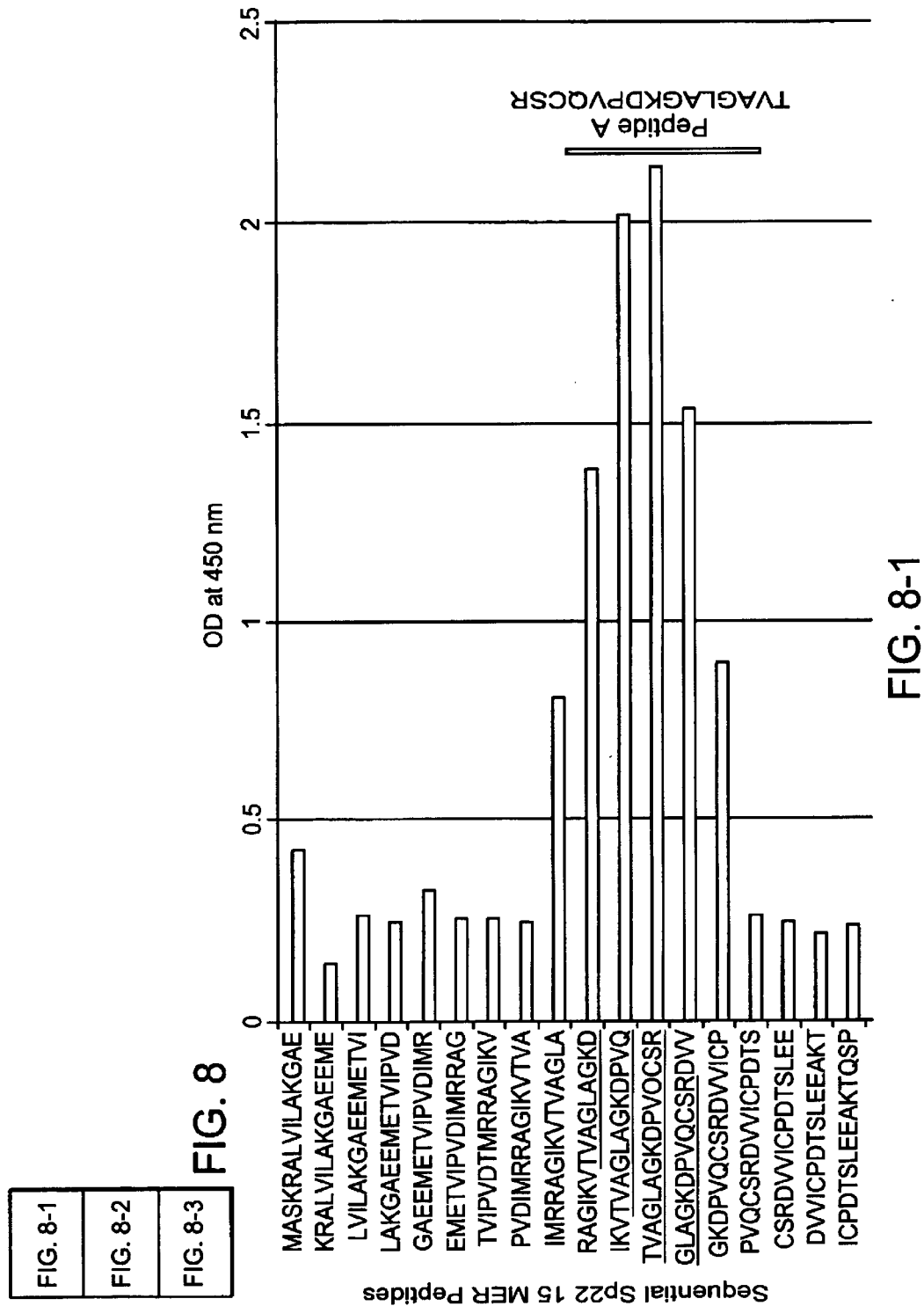

Fig. 10
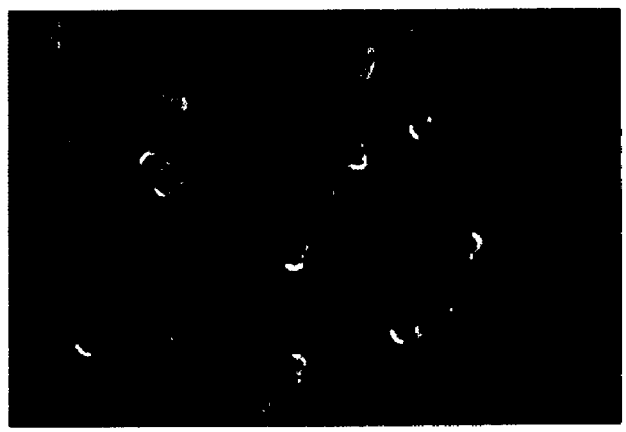

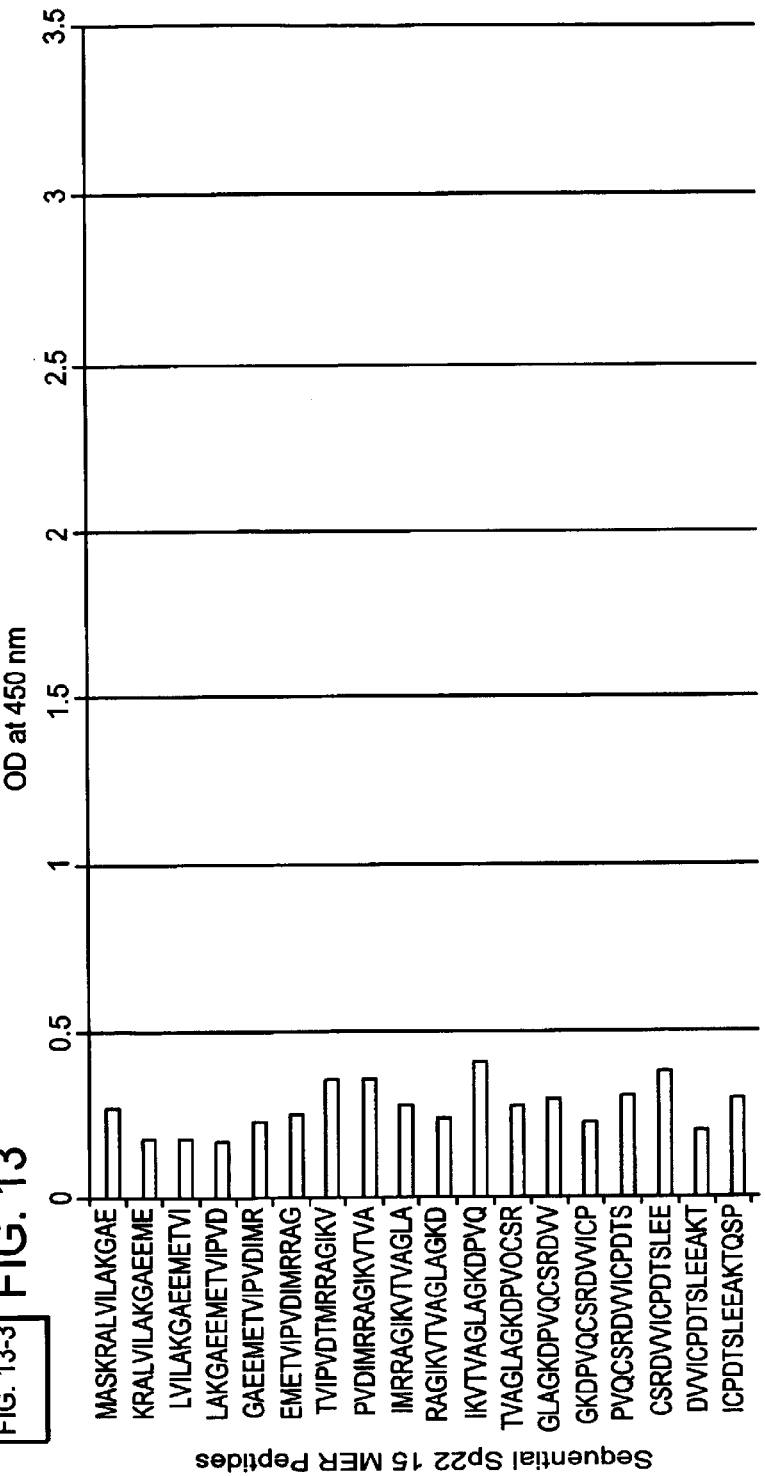

FIG. 15

```
  1    xxxxxxxxxxxxxxxxxxxxxxxxxxxxxxxxxxxxxxxxxatggcatccaaaagagctctggtcatc  66
  1     X  X  X  X  X  X  X  X  X  X  X  X  X  M  A  S  K  R  A  L  V  I   22
 67    ctagccaaaggagcagaggagatggagacagtgattcctgtggacatcatgcggcgagctgggatt 132
 23     L  A  K  G  A  E  E  M  E  T  V  I  P  V  D  I  M  R  R  A  G  I   44
133    aaagtcaccgttgcaggcttggctgggaaggaccccgtgcagtgtagccgtgatgtagtgatttgt 198
 45     K  V  T  V  A  G  L  A  G  K  D  P  V  Q  C  S  R  D  V  V  I  C   66
199    ccggataccagtctggaagaagcaaaaacacagggaccatacgatgtggttgttcttccaggagga 264
 67     P  D  T  S  L  E  E  A  K  T  Q  G  P  Y  D  V  V  V  L  P  G  G   88
265    aatctgggtgcacagaacttatctgagtcggctttggtgaaggagatcctcaaggagcaggagaac 330
 89     N  L  G  A  Q  N  L  S  E  S  A  L  V  K  E  I  L  K  E  Q  E  N  110
331    aggaagggcctcatagctgccatctgtgcgggtcctacggccctgctggctcacgaagtaggcttt 396
111     R  K  G  L  I  A  A  I  C  A  G  P  T  A  L  L  A  H  E  V  G  F  132
397    ggatgcaaggttacatcgcacccattggctaaggacaaaatgatgaacggcagtcactacagctac 462
133     G  C  K  V  T  S  H  P  L  A  K  D  K  M  M  N  G  S  H  Y  S  Y  154
463    tcagagagccgtgtggagaaggacggcctcatcctcaccagccgtgggcctgggaccagcttcgag 528
155     S  E  S  R  V  E  K  D  G  L  I  L  T  S  R  G  P  G  T  S  F  E  176
528    tttgcgctggccattgtggaggcactcagtggcaaggacatggctaaccaagtgaaggccccgctt 594
177     F  A  L  A  I  V  E  A  L  S  G  K  D  M  A  N  Q  V  K  A  P  L  198
595    gttctcaaagactagagagcccaagccctggaccctggaccccaggctgagcaggcattggaagc 660
199     V  L  K  D  *                                                       202
661    ccactagagagaccacagcccagtgaacctggcattggaagccactagtgtgtccacagcccagt 726
727    gaacctcaggaactaacgtgtgaagtagcccgctgctcaggaatctcgccctggctctgtactatt 792
793    ctgagccttgctagtagaataaacagttccccaagctc                              830
```

FIG. 16

| | | |
|---|---|---|
| 1 | gctgtgcagagccgtctggcagggttgacctcctaaagggatattccatctttattaatcattag | 65 |
| 66 | tagtgtggtcagagacttagcaccattggtctcccccaacctggtccagacatttcagcagttta | 130 |
| 131<br>1 | tcggaacagcaacaacagcaacaaaaccttcaaaatttacaagtctttaagaaatagaaATGgca<br>                                                                                                           M  A | 195<br>2 |
| 196<br>3 | tccaaaagagctctggtcatcctagccaaaggagcagaggagatggagacagtgattcctgtgga<br>  S   K   R   A   L   V   I   L   A   K   G   A   E   E   M   E   T   V   I   P   V   D | 260<br>24 |
| 261<br>25 | caccatgcggcgagctgggattaaagtcaccgttgcaggcttggctgggaaggacccgtgcagt<br>    I   M   R   R   A   G   I   K   V   T   V   A   G   L   A   G   K   D   P   V   Q | 325<br>45 |
| 326<br>46 | gtagccgtgatgtagtgatttgtccggataccagtctggaagaagcaaaaacacagggaccatac<br>  C   S   R   D   V   V   I   C   P   D   T   S   L   E   E   A   K   T   Q   G   P   Y | 390<br>67 |
| 391<br>68 | gatgtggttgttcttccaggaggaaatctgggtgcacagaacttatctgagtcggctttggtgaa<br>  D   V   V   V   L   P   G   G   N   L   G   A   Q   N   L   S   E   S   A   L   V   K | 455<br>89 |
| 456<br>90 | ggagatcctcaaggagcaggagaacaggaagggcctcatagctgccatctgtgcgggtcctacgg<br>  E   I   L   K   E   Q   E   N   R   K   G   L   I   A   A   I   C   A   G   P   T | 520<br>110 |
| 521<br>111 | ccctgctggctcacgaagtaggctttggatgcaaggttacatcgcacccattggctaaggacaaa<br>  A   L   L   A   F   E   V   G   F   G   C   K   V   T   S   H   P   L   A   K   D   K | 585<br>132 |
| 586<br>133 | atgatgaacggcagtcactacagctactcagagagccgtgtggagaaggacggcctcatcctcac<br>  M   M   N   G   S   H   Y   S   Y   S   E   S   R   V   E   K   D   G   L   I   L   T | 650<br>154 |
| 651<br>155 | cagccgtgggcctgggaccagcttcgagtttgcgctggccattgtggaggcactcagtggcaagg<br>    S   R   G   P   G   T   S   F   E   F   A   L   A   I   V   E   A   L   S   G   K | 715<br>175 |
| 716<br>176 | acatggctaaccaagtgaaggccccgcttgttctcaaagacTAGagagcccaagccctggaccct<br>  D   M   A   N   Q   V   K   A   P   L   V   L   K   D | 780<br>189 |
| 781 | ggaccccaggctgagcaggcattggaagcccactagtgtgtccacagcccagtgaacctggcat | 845 |
| 846 | tggaagcccactagtgtgtccacagcccagtgaacctcaggaactaacgtgtgaagtagcccgct | 910 |
| 911 | gctcaggaatctcgccctggctctgtactattctgagccttgctagtagaataaacagttcccca | 975 |

SEQUENCE LISTING

<160> NUMBER OF SEQ ID NOS: 4

<210> SEQ ID NO 1
<211> LENGTH: 189
<212> TYPE: PRT
<213> ORGANISM: Homo sapiens

<400> SEQUENCE: 1

```
Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Cys Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185
```

<210> SEQ ID NO 2
<211> LENGTH: 980
<212> TYPE: DNA
<213> ORGANISM: Rattus rattus

```
<220> FEATURE:
<221> NAME/KEY: CDS
<222> LOCATION: (190)..(756)
<223> OTHER INFORMATION:

<400> SEQUENCE: 2
gctgtgcaga gccgtctggc agggttgacc tcctaaaggg atattccatc tttattaatc      60
attagtagtg tggtcagaga cttagcacca ttggtctccc ccaacctggt ccagacattt     120
cagcagttta tcggaacagc aacaacagca acaaaacctt caaaatttac aagtctttaa     180 gaaatagaa atg gca tcc aaa aga gct ctg gtc atc cta gcc aaa gga gca    231
          Met Ala Ser Lys Arg Ala Leu Val Ile Leu Ala Lys Gly Ala
            1               5                  10 gag gag atg gag aca gtg att cct gtg gac atc atg cgg cga gct ggg      279
Glu Glu Met Glu Thr Val Ile Pro Val Asp Ile Met Arg Arg Ala Gly
 15              20                  25                  30 att aaa gtc acc gtt gca ggc ttg gct ggg aag gac ccc gtg cag tgt      327
Ile Lys Val Thr Val Ala Gly Leu Ala Gly Lys Asp Pro Val Gln Cys
                 35                  40                  45 agc cgt gat gta gtg att tgt ccg gat acc agt ctg gaa gaa gca aaa      375
Ser Arg Asp Val Val Ile Cys Pro Asp Thr Ser Leu Glu Glu Ala Lys
             50                  55                  60 aca cag gga cca tac gat gtg gtt gtt ctt cca gga gga aat ctg ggt      423
Thr Gln Gly Pro Tyr Asp Val Val Val Leu Pro Gly Gly Asn Leu Gly
         65                  70                  75 gca cag aac tta tct gag tcg gct ttg gtg aag gag atc ctc aag gag      471
Ala Gln Asn Leu Ser Glu Ser Ala Leu Val Lys Glu Ile Leu Lys Glu
     80                  85                  90 cag gag aac agg aag ggc ctc ata gct gcc atc tgt gcg ggt cct acg      519
Gln Glu Asn Arg Lys Gly Leu Ile Ala Ala Ile Cys Ala Gly Pro Thr
 95                 100                 105                 110 gcc ctg ctg gct cac gaa gta ggc ttt gga tgc aag gtt aca tcg cac      567
Ala Leu Leu Ala His Glu Val Gly Phe Gly Cys Lys Val Thr Ser His
                115                 120                 125 cca ttg gct aag gac aaa atg atg aac ggc agt cac tac agc tac tca      615
Pro Leu Ala Lys Asp Lys Met Met Asn Gly Ser His Tyr Ser Tyr Ser
            130                 135                 140 gag agc cgt gtg gag aag gac ggc ctc atc ctc acc agc cgt ggg cct      663
Glu Ser Arg Val Glu Lys Asp Gly Leu Ile Leu Thr Ser Arg Gly Pro
        145                 150                 155 ggg acc agc ttc gag ttt gcg ctg gcc att gtg gag gca ctc agt ggc      711
Gly Thr Ser Phe Glu Phe Ala Leu Ala Ile Val Glu Ala Leu Ser Gly
    160                 165                 170 aag gac atg gct aac caa gtg aag gcc ccg ctt gtt ctc aaa gac          756
Lys Asp Met Ala Asn Gln Val Lys Ala Pro Leu Val Leu Lys Asp
175                 180                 185 tagagagccc aagccctgga ccctggaccc ccaggctgag caggcattgg aagcccacta    816
gtgtgtccac agcccagtga acctggcatt ggaagcccac tagtgtgtcc acagcccagt    876
gaacctcagg aactaacgtg tgaagtagcc cgctgctcag gaatctcgcc ctggctctgt    936
actattctga gccttgctag tagaataaac agttccccaa gctc                     980

<210> SEQ ID NO 3
<211> LENGTH: 189
<212> TYPE: PRT
<213> ORGANISM: Rattus rattus
```

```
<400> SEQUENCE: 3

Met Ala Ser Lys Arg Ala Leu Val Ile Leu Ala Lys Gly Ala Glu Glu
1               5                   10                  15

Met Glu Thr Val Ile Pro Val Asp Ile Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Thr Ser Leu Glu Glu Ala Lys Thr Gln
    50                  55                  60

Gly Pro Tyr Asp Val Val Leu Pro Gly Gly Asn Leu Gly Ala Gln
65                  70                  75                  80

Asn Leu Ser Glu Ser Ala Leu Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Val Gly Phe Gly Cys Lys Val Thr Ser His Pro Leu
        115                 120                 125

Ala Lys Asp Lys Met Met Asn Gly Ser His Tyr Ser Tyr Ser Glu Ser
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Ser Gly Lys Asp
                165                 170                 175

Met Ala Asn Gln Val Lys Ala Pro Leu Val Leu Lys Asp
            180                 185

<210> SEQ ID NO 4
<211> LENGTH: 842
<212> TYPE: DNA
<213> ORGANISM: Rattus rattus
<220> FEATURE:
<221> NAME/KEY: CDS
<222> LOCATION: (52)..(618)
<223> OTHER INFORMATION:

<400> SEQUENCE: 4
tggcttcgcg tgggtggagg aggcgcggct gcaggtcttt aagaaataga a atg gca      57
                                                         Met Ala
                                                          1 tcc aaa aga gct ctg gtc atc cta gcc aaa gga gca gag gag atg gag     105
Ser Lys Arg Ala Leu Val Ile Leu Ala Lys Gly Ala Glu Glu Met Glu
      5                   10                  15 aca gtg att cct gtg gac atc atg cgg cga gct ggg att aaa gtc acc     153
Thr Val Ile Pro Val Asp Ile Met Arg Arg Ala Gly Ile Lys Val Thr
 20                  25                  30 gtt gca ggc ttg gct ggg aag gac ccc gtg cag tgt agc cgt gat gta     201
Val Ala Gly Leu Ala Gly Lys Asp Pro Val Gln Cys Ser Arg Asp Val
35                  40                  45                  50 gtg att tgt ccg gat acc agt ctg gaa gaa gca aaa aca cag gga cca     249
Val Ile Cys Pro Asp Thr Ser Leu Glu Glu Ala Lys Thr Gln Gly Pro
                55                  60                  65 tac gat gtg gtt gtt ctt cca gga gga aat ctg ggt gca cag aac tta     297
Tyr Asp Val Val Val Leu Pro Gly Gly Asn Leu Gly Ala Gln Asn Leu
            70                  75                  80 tct gag tcg gct ttg gtg aag gag atc ctc aag gag cag gag aac agg     345
Ser Glu Ser Ala Leu Val Lys Glu Ile Leu Lys Glu Gln Glu Asn Arg
        85                  90                  95
```

```
                                                                        -continued aag ggc ctc ata gct gcc atc tgt gcg ggt cct acg gcc ctg ctg gct        393
Lys Gly Leu Ile Ala Ala Ile Cys Ala Gly Pro Thr Ala Leu Leu Ala
    100                 105                 110 cac gaa gta ggc ttt gga tgc aag gtt aca tcg cac cca ttg gct aag        441
His Glu Val Gly Phe Gly Cys Lys Val Thr Ser His Pro Leu Ala Lys
115                 120                 125                 130 gac aaa atg atg aac ggc agt cac tac agc tac tca gag agc cgt gtg        489
Asp Lys Met Met Asn Gly Ser His Tyr Ser Tyr Ser Glu Ser Arg Val
                135                 140                 145 gag aag gac ggc ctc atc ctc acc agc cgt ggg cct ggg acc agc ttc        537
Glu Lys Asp Gly Leu Ile Leu Thr Ser Arg Gly Pro Gly Thr Ser Phe
            150                 155                 160 gag ttt gcg ctg gcc att gtg gag gca ctc agt ggc aag gac atg gct        585
Glu Phe Ala Leu Ala Ile Val Glu Ala Leu Ser Gly Lys Asp Met Ala
                165                 170                 175 aac caa gtg aag gcc ccg ctt gtt ctc aaa gac tagagagccc aagccctgga     638
Asn Gln Val Lys Ala Pro Leu Val Leu Lys Asp
        180                 185 ccctggaccc ccaggctgag caggcattgg aagcccacta gtgtgtccac agcccagtga     698
acctggcatt ggaagcccac tagtgtgtcc acagcccagt gaacctcagg aactaacgtg     758
tgaagtagcc cgctgctcag gaatctcgcc ctggctctgt actattctga gccttgctag     818
tagaataaac agttccccaa gctc                                            842
```

METHOD FOR EVALUATING AND AFFECTING MALE FERTILITY

The current application is a continuation-in-part of 09/123,492, filed Jul. 28, 1998, now U.S. Pat. No. 6,197,940, which claims the benefit of priority under 35 § USC 119(e) to U.S. provisional application 60/082,753, filed Apr. 23, 1998, said Ser. No. 09/123,492 is a continuation in part of PCT/US97/01725, filed Jan. 29, 1997, which is a continuation-in-part of Ser. No. 08/593,677, filed Jan. 29, 1996, now abandoned. Ser. Nos. 09/123,492 and 08/593,677 are hereby incorporated by reference in their entirety.

FIELD OF THE INVENTION

Background of the Invention

Sperm production in the testis of human males is far less efficient than sperm production in other mammals, such as rat, rabbit and monkey (Amann, 1970) due to an increased rate of germ cell atresia. Together with this is the fact that a high incidence of sperm in the ejaculate of a fertile man is morphologically abnormal (Wyrobek et al., 1982). Thus, there is a heightened awareness of the possibility that the quantity and quality of sperm in the ejaculates of men are declining because of environmental influences (Sharpe, 1993). A toxicant-induced alteration in the process of sperm maturation during sperm transit through the epididymis, the organ in which sperm acquire fertilizing ability, could render a man infertile. It has been hypothesized that specific proteins are added to sperm in the epididymis which confer fertility. Recently, Klinefelter et al., in *Journal of Andrology* 15(4), 318–327 (1994) demonstrated that an 18 kD epididymal sperm surface protein, presumably a plasma membrane protein, was well correlated with fertility, although it was not believed that this protein was predictive of fertility.

There continues to be great interest in developing new and improved contraceptives. New contraceptives should be superior to existing products, e.g., oral contraceptives used by millions of women over the last 30 years are not only safe and effective but even protect women against some cancers. However, other methods of contraception are still needed by many segments of the world's population, as many women do not have reliable access to oral contraceptives, or may suffer adverse reactions to the hormones use in oral contraceptives.

Additionally, fertility testing is becoming more widespread as increasing numbers of apparently infertile couples seek medical assistance in conception. Because reproductive abnormalities of both sexes may affect fertility, assessing male fertility is common in fertility evaluations. While the most common starting point for evaluation of male fertility is an assessment of the sperm count in semen, also important to fertility is sperm motility. Therefore, in male fertility analyses, sperm motility has also been a factor.

Currently available techniques for measuring sperm count and sperm motility are microscopic in nature. A quantitative evaluation of sperm morphology and motility requires substantial experience on the part of the laboratory technician. The high level of experience required by laboratory technicians precludes general office evaluation of semen samples and generally requires referral to a specialized laboratory. Even with adequate resources, debris in semen samples can cause erroneous or inconsistent results.

Attempts to develop biochemical assays of semen have not resulted in simple procedures which may be performed in either the physician's office or a dedicated semen evaluation lab. Most biochemical markers have failed to demonstrate correlations with sperm number, motility, or fertility. Activity of fumarase, an enzyme present in semen, has been found to correlate to both sperm count and percentage motility, Crabbe, *J. Reprod. Fert.* 51: 73–76 (1977). Crabbe measured fumarase activity by spectrophotometric measurements. Unfortunately, spectrophotometric assays are not generally suitable for office assays because of the cost of these specialized devices as well as the training required for accurate and reproducible operations.

Dorian, in U.S. Pat. No. 5,434,057, expanded on Crabbe's method by providing devices for assessing sperm number and motility in semen samples comprising a solid support having a carrier matrix containing a fumarase substrate and malate dehydrogenase. The sample is applied to the carrier matrix and a visual signal is detected from the solid support resulting from metabolism of the fumarase substrate by fumarase in the sample. While this assay detects motile sperm in a semen sample, there is not method for inhibiting fertility nor of selecting out the most fertile sperm in a sample.

Feuchter et al., in U.S. Pat. No. 5,250,417, disclose a method for detecting the ability of sperm to undergo the acrosome reaction to permit determination of the fertility of male mammals. The acrosome reaction is a process by which sperm release hydrolytic enzymes that degrade the zona pellucida, which must be penetrated to enable the sperm and ovum to come into contact, fuse, and complete the fertilization process.

In recent years, other studies have targeted different proteins associated with sperm in an attempt to provide new contraceptive alternatives. Major research efforts involve immunological approaches to fertility control. The development of contraceptive vaccines is directed towards the immunoneutralization of reproductive processes or interfering with fertilization by inducing antibodies against oocytes and spermatozoa. Several sperm antigens shown to have high immunocontraceptive potential are human sperm membrane antigen (SP-10) and guinea pig sperm membrane protein (PH-20). SP-10 is a sperm membrane specific antigen of 24–24 kD which was isolated using a monoclonal antibody (MHS-10) that cross-reacts with the entire acrosomal region. It is associated with the outer aspect of the inner acrosomal membrane and the inner aspect of the outer acrosomal membrane of mature human sperm. It has been reproduced recombinantly in an *Escherichia coli* expression system.

PH-20, a guinea pig sperm protein of 64 kD, is present on both the plasma membrane and inner acrosomal membrane of sperm. It is essential for adhesion of sperm to the zona pellucida, the initial step in the fertilization process. Active immunization with PH-20 causes infertility in both male and female guinea pigs for a period ranging from six to fifteen months.

O'Rand et al., in U.S. Pat. No. 5,175,148, disclose a sperm antigen corresponding to a sperm autoantigenic epitope which can be used as immunocontraceptive agent as well as for diagnosing autoimmune infertility. The synthetic peptide corresponds to an autoantigenic epitope of rabbit sperm membrane autoantigen.

Several other antigens with good immunocontraceptive potential have been identified and investigated in laboratory animals, including lactic dehydrogenase-x, an isoenzyme of lactic dehydrogenase confined to male germ cells. A synthetic peptide based upon a portion of this antigen has been shown to reduce fertility in laboratory animals.

Unfortunately, most studies have found that the rate and duration of the immunocontraceptive effects are less than acceptable. A problem in immunological approaches to antifertility research is the need for a safe, effective adjuvant and suitable animal models for evaluating the efficacy and safety of methods.

Although most contraceptive research has been directed to use in females, there is an interest in male fertility control both from a scientific as well as a biological viewpoint. Many compounds have been identified as having male antifertility activity in various species, e.g., gossypol, 5-thio-D-glucose, and 6-chlorodeoxyglucose. Studies have also been conducted on the use of androgens to control male fertility. Unfortunately, most compounds identified as useful in controlling male fertility appear either to have irreversible antifertility effects, to be inherently toxic, or to affect libido. It has been demonstrated that sperm count could be depressed in men injected with large doses of androgens. However, there are still questions about the potential utility of androgens as male antifertility agents. The ideal male contraceptive would produce azoospermia without compromising libido or sexual potency, and would be reversible.

While numerous sperm proteins (Primakoff et al., 1997; Burks et al., 1995; Wei et al., 1994; o'Rand et al., 1984; Lea et al., 1996; O'Rand et al. 1996; Amman et al., 1998a,b; Hammerstedt et al., 1997; Cohen et al., 1996) as well as seminal plasma proteins (Killian et al., 1996; Peknicova et al., 1997) have been associated with fertility over the years, in most cases they have been identified based on the demonstration of sperm-egg binding in vitro, a system that differs considerably from the natural environment of sperm.

In recent years several proteins have been linked in some way or another to fertilizing capacity of sperm. While most of these proteins are associated with the sperm membrane, some have been identified in seminal plasma. Two of the sperm proteins are quite large. The first of these is a 64 kD sperm membrane protein (PH-20) which was found to localize over the arosome of guinea pig sperm and believed to function during fertilization (Hunnicutt et al., 1996). Antibody to PH-20 has been shown to prevent binding of sperm to the zona pellucida, and males were rendered infertile when PH-20 was administered as an immune vaccine (Primakoff et al., 1997). However, PH-20 has only been described in the guinea pig, and the PH-20 vaccine severely compromises spermatogenesis in older animals, rendering the effect irreversible. In addition, a 95 kD mouse sperm protein was identified as a phosphotyrosine protein ligand for ZP3, a glycoprotein in the extracellular matrix of the egg (Burks et al., 1995). Specific peptide fragments of this protein blocked binding of sperm to the zone pellucida in vitro, but inhibition of fertility in vivo has not been demonstrated.

Several small sperm proteins have been linked to fertility. Rabbit sperm autoantigen I (RSAI), now referred to as SP-17 (Lea et al., 1996), is a 24 kD protein unique to the testis. This protein appears to be common to rabbit, mouse, and humans, as evidenced by cDNA sequence homology. Monospecific antibodies to this protein have not been used to demonstrate antifertility effects in vivo. There is no protein homology based on cDNA and deduced amino acid sequence between SP-17 and SP22.

Protein D and E are secreted by the epithelium of the epididymis. These proteins have been linked to fertility as the plasma membrane fo the oocyte exposes protein D/E binding domains during sperm-egg fusion (Cohen et al., 1996). Antibody directed against the D/E complex significantly inhibited sperm penetration of zona-free eggs in vitro (Cuasnicu et al., 1990), but no fertility role has yet been demonstrated in vivo. While these proteins have molecular weights of 26 and 32 kD, respectively, the sequence of SP22, the protein of the present invention, is not related to that of proteins D or E.

Wei et al., 1994, recovered a 17 kD protein from a detergent extract of human sperm. Antibody to this glycoprotein localized over the head of sperm multiple species, but staining was localized over the entire head of the sperm as well as over the principal piece of the tail of the sperm, suggesting a lack of specificity. Thus, while the antibody inhibited fertility in vivo, much of this inhibition appears to result from nonspecific binding. Unfortunately, adequate control data were not shown. The 17 kD protein described by Wei et al. (1994) was never identified in the profile of proteins in the original detergent extract. Thus, it is impossible to determine the relationship of this protein relative to others reported in the literature. It seems that this may be similar to the more recently-described SP-17 described by Lea et al., 1996, but this is impossible to determine, as Wei et al. did not provide amino acid sequence data.

O'Rand et al. described DNA encoding a mammalian Sp17 protein or antigenic peptides which are fragments thereof. These proteins and fragments are said to be useful as immunocontraceptive agents and for diagnosing autoimmune fertility.

Two proteins identified in the seminal fluid, the sperm-free fraction of semen, have been linked to fertility. The first is a 17 kD protein referred to as ACR.3 (Capkova and Peknicova, 1997). This protein is a coating protein rather than an integral membrane protein and is apparently involved in mediating sperm binding to the zona pellucida, as addition of purified ACR.3 to normal sperm actually diminishes their capacity to bind to the zone. The function of these seminal plasma proteins may be to prevent premature capacitation and binding of sperm to the egg. Such membrane stabilizers may be critical to normal fertilization in vivo, but are not diagnostic of fertilizing potential. In fact, antibody to ACR.3 does not inhibit fertilization. The second seminal plasma protein that has been associated with the fertility of bull sperm is a 265 kD protein (Killian et al., 1996), now known as prostaglandin D-synthase (Gerena et al., 1998). This protein may have more direct influence on fertility, as the addition of seminal plasma from higher fertility bulls increased the ability of sperm from lower fertility bulls to penetrate the egg in vitro. However, neither the direct addition of purified 26 kD protein, nor in vivo function tests, have been performed.

SUMMARY OF THE INVENTION

It is an object of the present invention to overcome the aforesaid deficiencies in the prior art.

It is another objection of the present invention to provide a means for predicting male fertility in animals as well as in human males.

It is another object of the present invention to screen for environmental endocrine disruptors, as endocrine disruption can lead to male-mediated infertility.

It is yet another object of the present invention to screen animals and humans exposed to known or suspected endocrine disruptors for fertility.

It is still another object of the present invention to select sires for artificial insemination who are good candidates for providing sperm for insemination.

It is a further object of the present invention to screen human semen for fertility prior to undertaking assisted reproductive technology techniques to improve the success of these techniques.

It is a further object of the present invention to improve fertility in males who fail to express a sufficient amount of SP22, formerly known as SP-16, in sperm.

It is another object of the present invention to provide a reversible male contraceptive.

It has been found that a 22 kD sperm protein, SP22, formerly identified as SP-16, is very significantly correlated with fertility (p<0.0001; N=52) and predictive of fertility. If an antibody to this protein is generated, the degree of antibody recognition by sperm in an epididymal sperm sample or ejaculate would reflect the fertility of the sample. This antibody can be used as a contraceptive to block the expression of SP22 to render sperm infertile, screen for toxicity, select superior sires for artificial insemination, and select men for assisted reproductive technologies. The protein itself can be used as a contraceptive vaccine, inactivated by gene knockout, or the protein can be added to sperm from infertile men to make fertility techniques more feasible.

SP22 is unique compared to any putative fertility proteins previously identified in either sperm or seminal plasma. Moreover, a search of the gene database failed to reveal any previously identified protein in male reproductive biology that has any homology with SP22. Both the amino acid homologous with DJ-1 (Nagakubo et al., 1997), a protein for which an oncogene role was speculated. These investigators have since abandoned this notion, and, to date, no definitive role exists for DJ-1.

The protein SP22, based upon initial electrophortic runs, was originally thought to be a 16 kD protein, with a pI of 5.5, and was so identified in great-grandparent application Ser. No. 08/593,677. However, after comparing several types of molecular weight standards, the molecular weight of this protein was found consistently to have an apparent molecular weight of 22 kD in 11% acrylamide gels. For purposes of the present invention, the protein will be identified as SP22, although in the great-grandparent application U.S. Ser. No. 08/593,677, the protein was identified as SP-16.

BRIEF DESCRIPTION OF THE DRAWINGS

FIG. 1 compares the amino acid sequence of SP22 and DJ-1, and illustrates the four peptides identified following Edman degradation that were used to identify the homology with DJ1 and correct sequences of these peptides as they exist in SP22.

FIG. 6 graphs show the relationship of fertility vs. SP22 following exposure to epididymal toxicants (top) and testicular toxicants (bottom). It should be noted that the biphasic, threshold relationship is maintained regardless of the type of insult.

FIG. 7 shows data from 131 animals representing the association between SP22 and fertility. These data were pooled from a number of toxicology studies, in which testicular toxicants or epididymal toxicants were tested.

FIGS. 10A–C are micrographs depicting immunolocalization of SP22 on fresh, unfixed rat cauda epididymal sperm (A) in the presence of anti-SP22 peptide Ig only (1:200); (B) in the presence of anti-SP22 peptide Ig+Peptide A (20 micrograms); and (C) in the presence of anti-SP22 peptide Ig+Peptide B (20 micrograms). It should be noted that the 15 amino acid sequence of Peptide A competes effectively with the Ig, indicating that Peptide A is an exposed domain.

FIG. 15 shows the nucleotide and amino acid sequences of SP22.

FIG. 16 shows the longer 5' untranslated regions of SP22A.

DETAILED DESCRIPTION OF THE INVENTION

Figure 3:
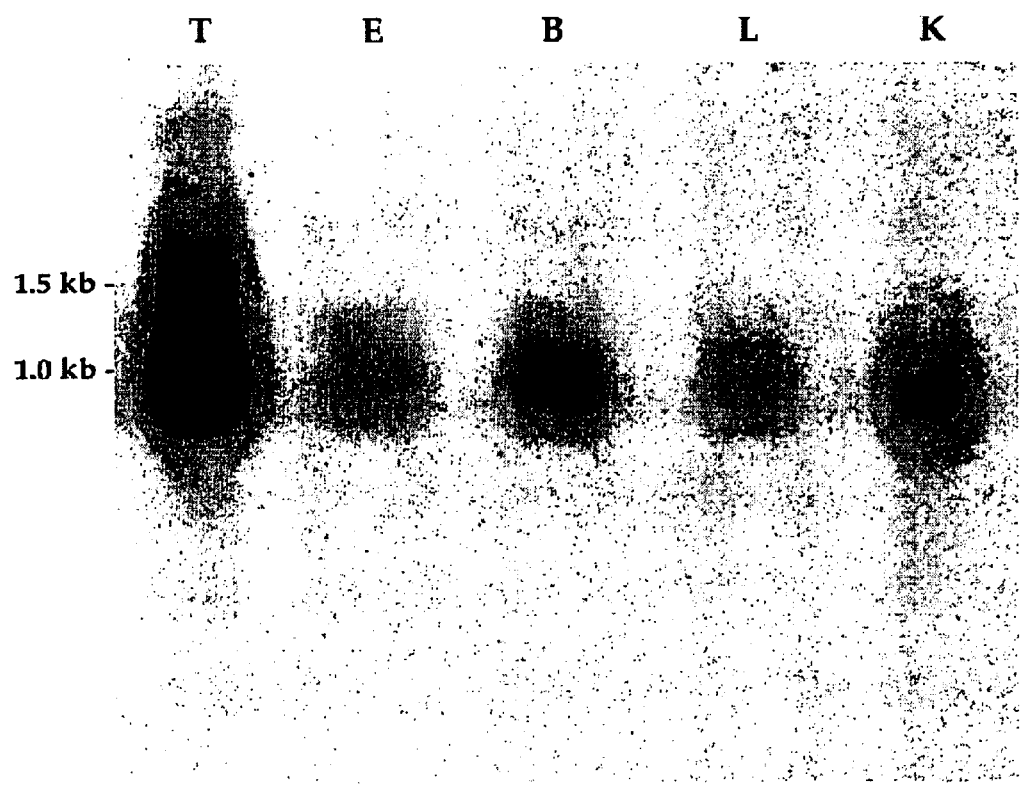
FIG. 3 shows a Northern blot showing the distinct higher (approximately 1.5 kB) molecular weight band of the SEQ ID NO:2 SP22A mRNA in the testis.

SP22 is characterized by the nucleotide and amino acid sequences of FIG. 15.

As noted previously, a number of proteins associated with the sperm membrane, including PH-20, ZP3, SP-17, and proteins D and E, as well as the Wei 17 kD protein, do not localize. In contrast, antibody to SP22 peptides localizes over a very discrete region of the sperm head, i.e., the ventral anterior surface of the equatorial segment. More importantly, however, the 17 kD protein described by Wei et al., (1994) was never identified in the profile of proteins in the original detergent extract. Thus, it is impossible to determine the relationship of this protein relative to others reported in the literature. It seems that this may be similar to the more recently-described SP-17 (Lea et al., 1996), but this is impossible to determine, as amino acid sequence data were not provided by Wei et al. (1994).

It is clearly evident that SP22 is unique compared to any putative fertility proteins previously identified in either sperm or seminal plasma. Moreover, a search of the gene database failed to reveal any previously identified protein in male reproductive biology that has any homology with SP22.

The presence of SP22 sequences with divergent 5' ends was not unexpected. Northern blotting of rat tissue RNAs, including testis, detected a 1 kB mRNA in all tissues and an additional 1.5 kB transcript found only in the testis. While a specific tissue of cell type has not been assigned to each sequence at this time, the unique 5' untranslated region of SP22 shows some similarity to the 5] untranslated region of mouse somatic expressed tag sequences homologous with rat SP22. Similarly, the longer 5' untranslated regions of SP22A, shown in FIGS. 2 and 16, suggested that encodes the 1.5 kB mRNA. This unique untranslated sequence may serve to impart mRNA stability for the subsequent expression of SP22 in the testis. Northern blotting with sequence specific probes is needed to relate the different SP22 sequences to their respective mRNAs and to their relative tissue abundance.

A short five-day exposure paradigm and multiple epididymal toxicants were used in an initial study which identified SP22 (Klinefelter et al., 1997). However, the discovery that SP22 originates in the testis prompted a study in which animals were exposed for 14 days to a testicular toxicant, bromochloracetic acid, which is a by-product of drinking water disinfection on which the U.S. Environmental Protection Agency has requested studies, as it is one of the more prevalent disinfection by-products in drinking water. Previous studies on dibromoacetic acid (Linder et al., 1995, 1997) and dichloroacetic acid (linder et al., 1997) revealed that the di-substituted haloacetic acids perturbed spermatogenesis, and that within fourteen days, defects (i.e., alterations in sperm motion and morphology) were manifest in epididymal sperm. Therefore, it was hypothesized that bromochloroacetic acid would act similarly.

SP22 levels on sperm were not evaluated in early haloacetic acid studies. Both a quantitative evaluation of SP22 in extracts of epididymal sperm and fertility following in utero insemination was incorporated in a recent study of bromochloroacetic acid. It was observed that SP22 levels were diminished in detergent extracts of epididymal sperm in a dose-related manner, with significance achieved at even the lowest dosage. Moreover, the fertility of sperm from the treated rats was significantly decreased and was highly correlated ($r^2$=0.90) with the SP22 levels.

Thus, it has now successfully been demonstrated that SP22 levels on epididymal sperm are compromised by chemicals which compromise both testicular and epididymal function. This established the feasibility of and an SP22-based assay of epididymal and ejaculated sperm as a diagnostic indicator of compromised sperm quality, i.e., fertility, in either toxicological or epidemiological settings. Additionally, the existence of SP22 on ejaculated sperm from multiple species (i.e., bull, stallion, human) established the feasibility of using such an SP22-based diagnostic to evaluate the fertility of sperm from these species when artificial breeding, herd sires, and assisted reproductive technologies (in vitro fertilization vs. in utero insemination) are considered. This is also of particular importance in breeding endangered species.

As indicated above during discussion of the 95 kD phosphotyrosine protein discovered on the mouse sperm membrane, specific peptides inherent to this protein were able to block the binding of sperm to the zona pellucida of the egg. Presumably, these peptides competed for binding of native sperm protein. More recently, Amann et al. (1998a, b) have used small peptides comprising the saposin subunits of the prosaposin or SGP-1 protein to enhance binding of sperm to an egg membrane substrate. In this assay, increased sperm binding indicated increased fertilizing ability.

In the present studies, highly specific SP22 IgG was used to negate the fertility of sperm in vivo. Since the epitope recognized by this IgG represents 15 and 8 amino acid peptide sequences of SP22, it can be reasoned that similar site-directed, small molecule recognition has been achieved. Moreover, it seems that one or both of these peptide targets may be pivotal in the function of SP22. Thus, these and other site-directed antagonists or agonists might serve to modulate (i.e., abate or enhance) the fertility of sperm.

The sperm protein SP22 is completely novel to the field of reproductive biology. SP22 is synthesized in the testis and can be recovered from testicular sperm before they enter the epididymis. SP22 is an integral component of the sperm membrane, and is a component of ejaculated sperm from other species including bull, stallion, and human. SP22 is highly correlated with fertility following exposure to testicular toxicants as well as epididymal toxicants. Moreover, SP22 is a causal modulator of fertility, as anti-SP22 peptide IgG can effectively block the fertility of sperm.

Since characteristic sequences of SP22 are known, it is possible to prepare functional derivatives of SP22 as well. By "functional derivative" is meant a fragment, variant, analog, agonist, or chemical derivative of SP22, which terms are defined below.

A "functional derivative" retains at least a portion of the amino acid sequence of SP22, which permits its utility in accordance with the present invention, namely, determining or affecting male fertility. A "fragment" of SP22 refers to any subset of the SP22 molecule, that is, a shorter peptide. The fragments of interest are those which can be used to determine or affect male fertility.

A "variant" of SP22 refers to a molecule which is substantially similar to either the entire SP22 protein or fragment thereof. Variant peptides may be covalently prepared by direct chemical synthesis of the variant peptide, using methods well known in the art.

Alternatively, amino acid sequence variants of SP22 can be prepared by mutation in the DNAs which encode the synthesized SP22. Such variants include, for example, deletions from, or insertions or substitutions of, residues within the amino acid sequence. Any combination of deletion, insertion, and substitution may also be made to arrive at the final constructs, provided that the final construct possesses the desired activity. Obviously, the mutations that will be made in the DNA encoding the variant peptide must not alter the reading frame and preferably will not create complementary regions that could produce secondary mRNA structure (cf. European Patent Publication No. EP 75,444).

At the generic level, these variants ordinarily are prepared by site-directed mutagenesis, as exemplified by Adelman et al., DNA 2: 183, 1983, of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of SP22 refers to a molecule which is substantially similar to either the entire molecule or a fragment thereof. The analog may be prepared by chemical synthesis.

A "chemical derivative" of SP22 contains additional chemical moieties not normally part of the SP22 amino acid sequence. Covalent modifications of the amino acid sequence are included within the scope of this invention. Such modifications may be introduced into the SP22 by reacting targeted amino acid residues of the peptide with an organic derivatizing agent that is capable of reacting with selected side chains or terminal residues.

Amino terminal residues can be reacted with succinic or other carboxylic acid anhydrides. Other suitable reagents for derivatizing alpha-amino-containing residues include amidoesters such as methyl picolinimidate; pyridoxal phosphate; pyridoxal; chloroborohyride; trinitrobenzenesulfonic acid; O-methylisourea; 2,4-pentanedione; and transaminase-catalase reacted with glyoxylate.

Specific modifications of tyrosyl residues per se have been studied extensively, with particular interest in introducing spectral labels into tyrosyl residues by reaction with aromatic diazonium compounds or tetranitromethane. Most commonly, N-acetylimidazole and tetranitromethane are use to form O-acetyl tyrosyl species and 3-nitro derivatives, respectively.

Carboxyl side groups such as aspartyl or glutamyl are selectively modified by reaction with carbodiimides (R=N—C—N—R=) such as 1-cyclohexyl-3-[2-morpholinyl-(4-ethyl)] carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

As used herein, the term "muteins" or "variants" refers to analogs of SP22 in which one or more of the amino acid residues of the natural SP22, preferably 1–10, and more preferably 1–5, residues, or even only a single residue, are replaced by different amino acid residues or are deleted, or one or more amino acid residues, such as 1–10, 1–5, or only one residue are added to the natural sequence of SP22. These muteins are prepared by known synthesis techniques and/or site-directed mutagenesis techniques, or by any other known technique suitable therefor. The substitutions are preferably conservative, see, e.g., Schulz et al., *Principle of Protein Structure*, Springer-Verlag, New York, 1978; and Creighton, *Proteins: Structure and Molecular Properties*, W. H. Freeman & Co., San Francisco, 1983; both of which are hereby incorporated by reference in their entireties.

Figures 2, 13:
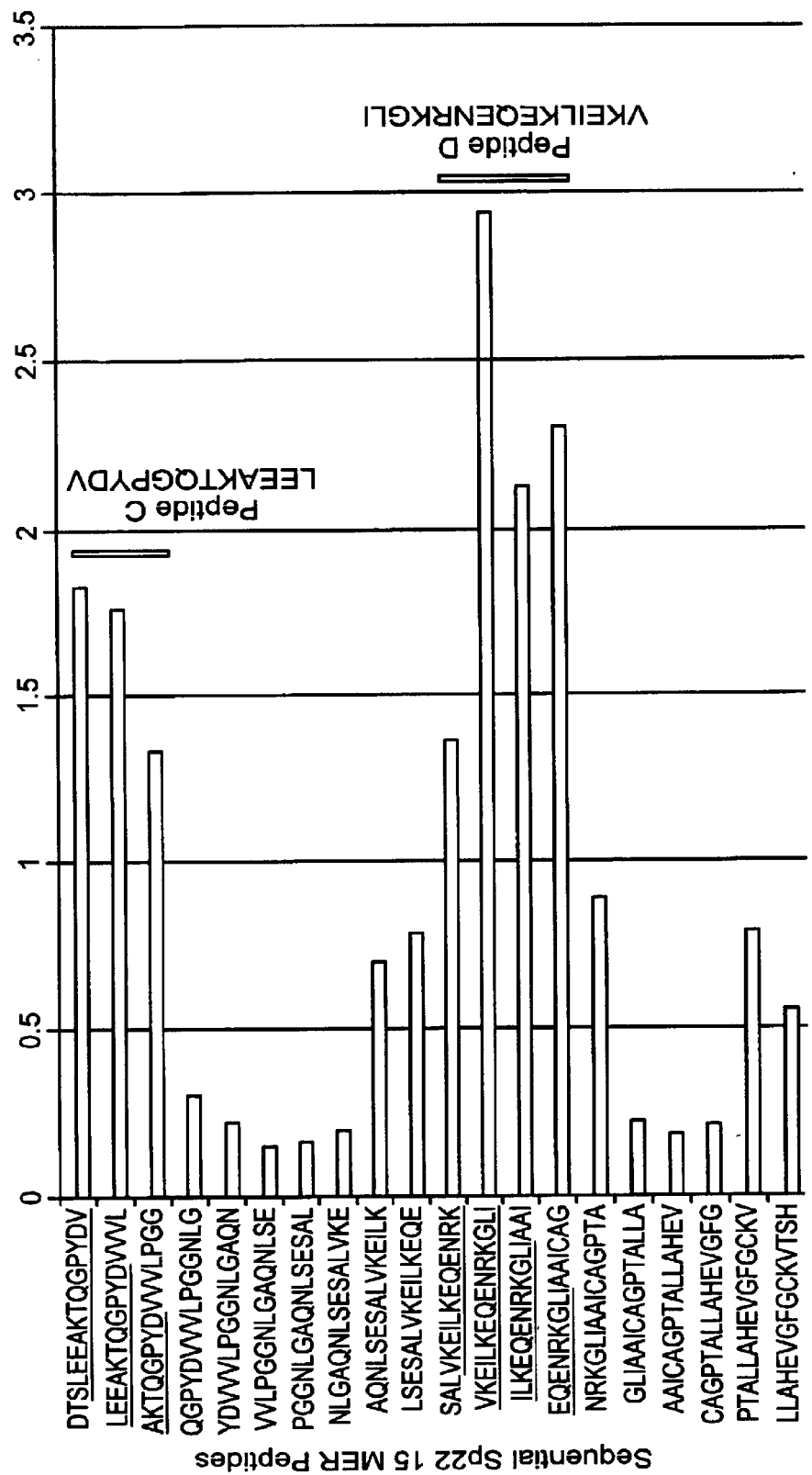
FIG. 13 is a plot illustrating the immunoreactivity of overlapping 15 mer PS-22 peptides with affinity-purified anti-recombinant SP22 Ig. Antiserum was affinity-purified and diluted 1:100 prior to use. The three reactive peaks within the 189 amino acid SP22 sequence are: Peptide C (LEEAKTQGPYDV), Peptide D (VKEILKEQENRKGLI), and Peptide E (GFGCKVTSHPLAKDK).
Figures 3, 13:
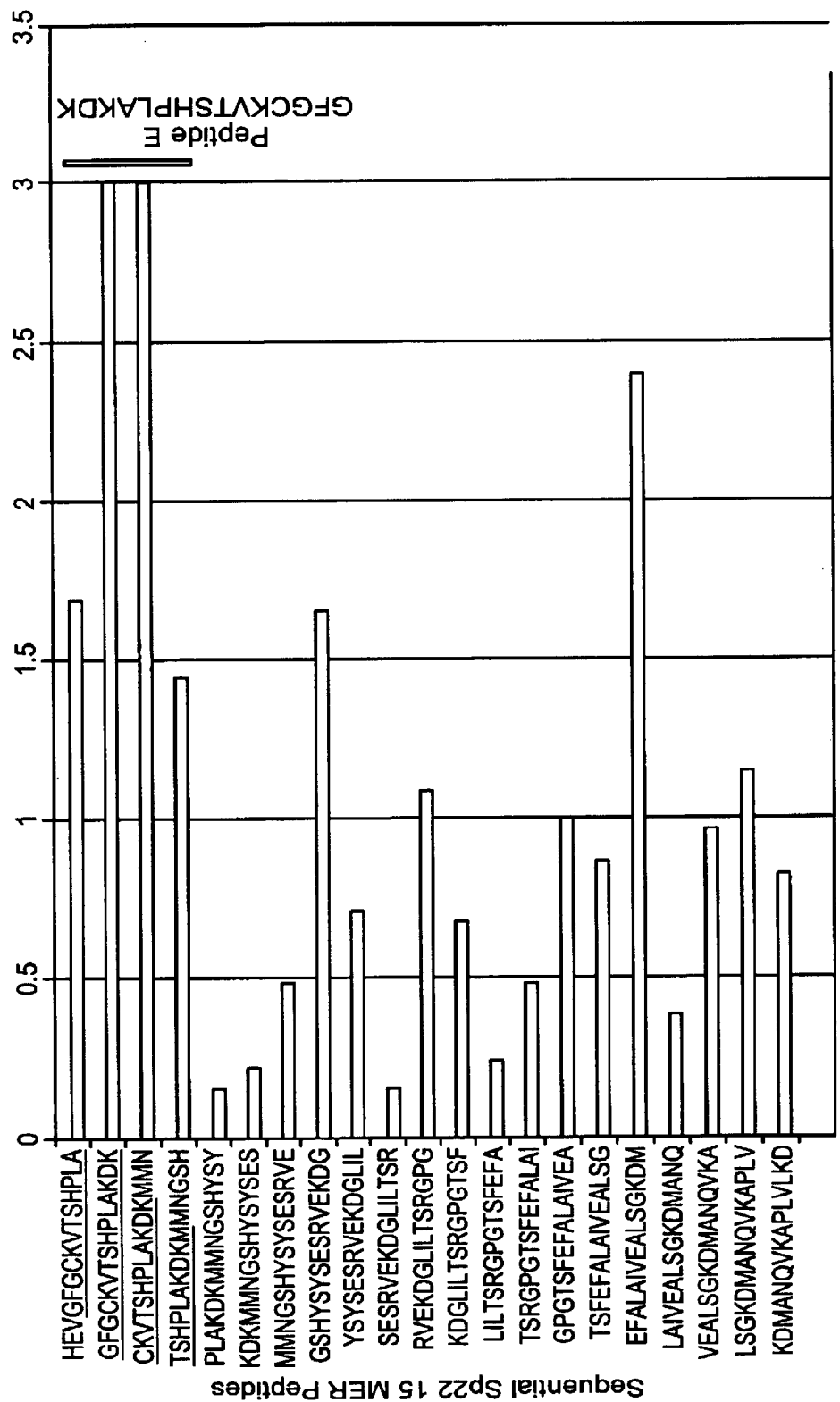

The types of such substitutions which may be made in the protein or peptide molecules of the present invention may be based on analysis of the frequencies of amino acid changes between a homologous protein of different species, such as those presented in Table 1–2 of Schulz et al., op. cit., and FIG. 3–9 of Creighton, op. cit. Based upon such analysis, conservative substitutions may be defined herein as exchanges within one of the following five groups:

I. Small aliphatic, nonpolar or slightly polar residues:
  Ala, Ser, Thr, Pro, Gly
II. Polar, negatively charged residues and their amides:
  Asp, Asn, Glu, Gln
III. Polar, positively charged residues:
  His, Arg., Lys
IV. Large, aliphatic nonpolar residues:
  Met, Leu, Ile, Val, Cys
V. Large aromatic residues:
  Phe, Try, Trp Within the foregoing groups the following five substitutions are considered "highly conservative":
  Asp/Glu
  His/Arg/Lys
  Phe/Tyr/Trp
  Met/Leu/Ile/Val Semi-conservative substitutions are defined to be exchanges between two of groups (I)–(V) above which are limited to supergroup (A), comprising (I), (II), and (III) above, or to supergroup (B), comprising (IV) and (V) above. Substitutions are not limited to the genetically encoded, or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues Functional Fragments Functional fragments of the SP22 molecule can be identified using a three-tiered anlysis, the first of which is identification of linear epitopes by mimotope analysis. For this, the 189 amino acids comprising SP22 were subdivided into 59 overlapping 15 amino acid peptides, with each peptide overlapping by three amino acids. The 59 peptides were biotinylated and allowed to bind to streptavidin-coated wells in 96-well plates. The reactivity of various antisera was detected by enzyme-linked immunosorbent assay (ELISA). Briefly, after care was taken to block non-specific binding, SP22 antibody was added sequentially (i.e., either affinity-purified anti-peptide Ig or affinity-purified full-length recombinant SP22 Ig), was added followed by sequential addition of peroxidase-conjugated secondary antibody, and peroxidase substrate. The optical density of each well was read at 450 nm and duplicate wells were averaged. The average value obtained from a similar ELISA using control serum (i.e., preimmune serum) was subtracted from the test Ig values and the resultant values were plotted to determine which linear epitopes were recognized by the Ig (cf. FIGS. 9 and 13, which represent the mimotope analysis for the antipeptide Ig and recombinant SP22 Ig, respectively).

The second and third components in the strategy to identify functional fragments of SP22 rely on the synthesis of non-biotinylated peptides corresponding to the epitopes (peptides) predicted by the mimotope analysis. To determine whether any of the epitopes recognized by mimotope analysis are actually exposed on the surface of the sperm membrane, i.e., represents an exposed domain, immunocytochemical staining with the Ig, without and with each of the peptides, was performed. For the anti-peptide Ig, immunostaining was completely ablated when peptide A was coincubated with the Ig. However, when peptide B was incubated with the Ig, staining remained identical to the staining observed with the Ig alone, as shown in FIG. 10. Since we know from the mimotope analysis that the antipeptide Ig recognizes both peptides, one can conclude that the 15 amino acid sequence of peptide A is an exposed domain, while the 8 amino acid sequence of peptide B is not exposed.

Figure 12:
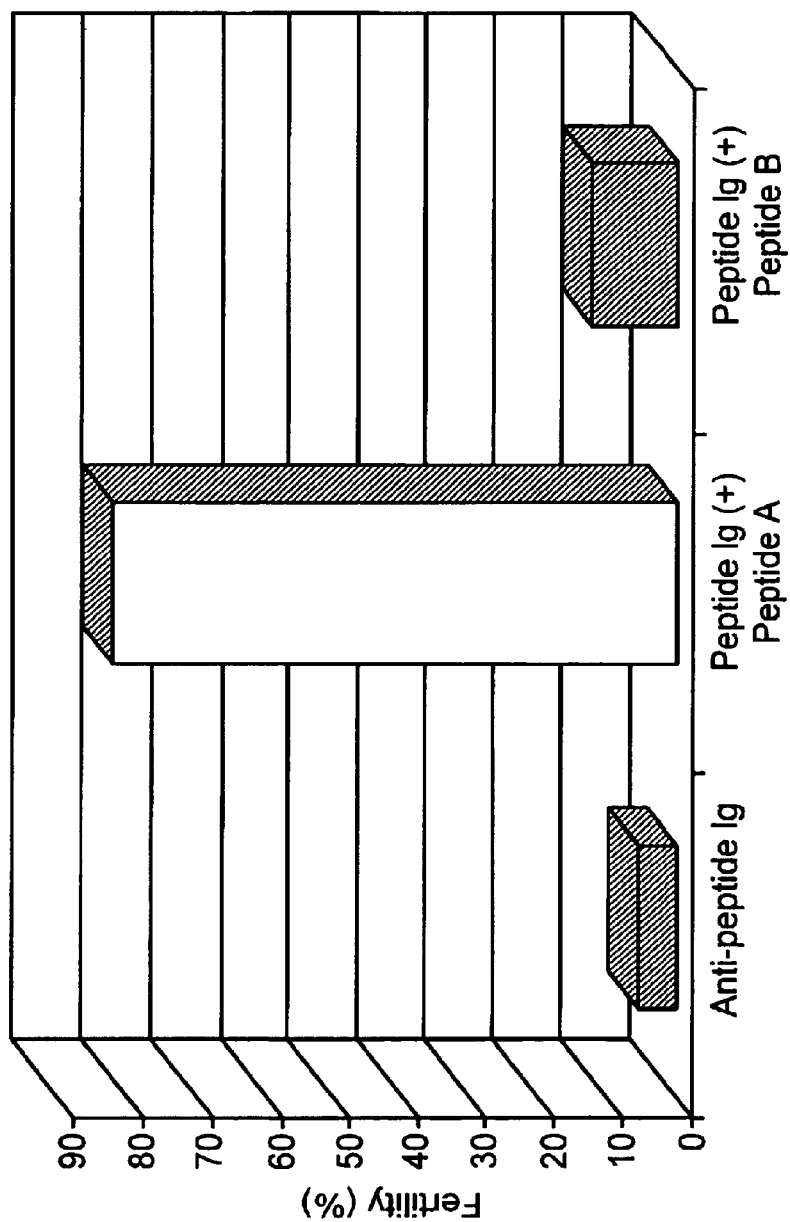
FIG. 12 is a graph depicting fertility of cauda epididymal rat sperm following in utero insemination when anti-SP22 peptide Ig alone is incubated (1:50) with the sperm five minutes prior to insemination, when Peptide A (20 micrograms) is coincubated with the Ig and sperm prior to insemination, and when Peptide B (20 micrograms) is coincubated with the Ig and sperm prior to insemination. It should be noted that the addition of Peptide A completely negated the Ig-induced inhibition of fertility, while addition of Peptide B had no significant effect on the Ig-induced inhibition of fertility.

The third component of the strategy is predicated on the hypothesis that only epitopes having exposed domains play functional roles in fertility. To test this, cauda epididymal sperm were inseminated in utero following incubation with Ig alone, or incubation with Ig and individual peptides (i.e., peptide A and peptide B). Indeed, while the anti-peptide Ig almost completely inhibited fertility, coincubation of Ig and peptide A resulted in no alteration in fertility relative to historical values. In contrast therewith, coincubation of anti-peptide Ig and peptide B also resulted in near complete inhibition of fertility, as shown in FIG. 12.

Collectively, these data clearly demonstrate that the exposed 15 amino acids of Peptide A represent a functional fragment of the SP22 molecule. In a similar fashion, any peptide can be assayed to determine if it, too, is a functional fragment of SP22.

Figure 14:
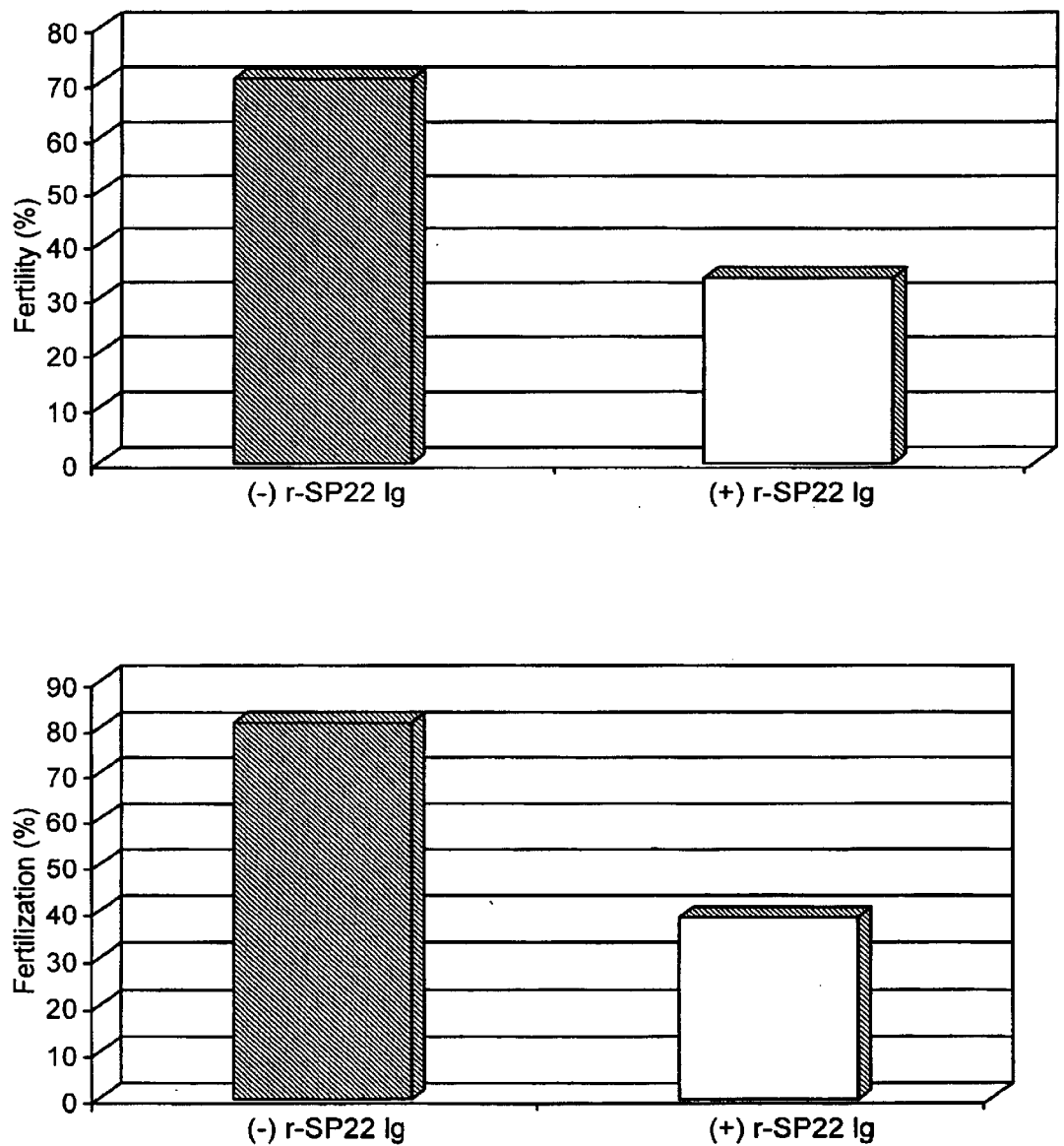
FIG. 14 is a graph depicting both in vivo and in vitro fertility results using affinity-purified anti-recombinant SP22 Ig. When rat cauda epididymal sperm were not incubated with Ig prior to in utero insemination, fertility was 71%. In contrast thereto, fertility was significantly reduced to 34% when recombinant SP22 Ig (1:50) was added five minutes prior to in utero insemination. The ability of the antibody to recombinant SP22 to inhibit fertility was confirmed by rat in vitro fertilization. Approximately 70% of the eggs were fertilized, as indicated by the presence of a sperm tail within the vitillus, after overnight incubation of cauda epididymal sperm in the absence of Ig. In contrast thereto, only 39% of the eggs were fertilized when sperm were incubated in the presence of anti-recombinant SP22 Ig (1:50). Interestingly, while this antibody has been used to confirm that SP22 is primarily restricted to the equatorial segment of sperm (cf. Klinefelter and Welch, 1999), the distinguishing difference appears to be a significant reduction in the number of sperm binding to the zona pellucida of the egg.

Based on work with Ig to the full length recombinant SP22, it can be reasoned that other functional fragments exist. First, the mimotope analysis of the recombinant SP22 Ig shown in FIG. 13 reveals three peptide epitopes. Second, the Ig to the recombinant SP22 immunostains sperm of all species tested (rat, bull, rabbit, hamster, and human; data for rat, bull, and human have been shown by Klinefelter and Welch, 2000). Third, this Ig inhibits fertility both in vivo and in vitro as shown in FIG. 14. As indicated above, any fragments can readily be tested without undue experimentation to identify those fragments which modulate fertility. Targeting functional fragments is likely to effectively reduce fertility to 0% and makes the use of site-directed antagonists more feasible across many species, including humans.

Antibodies that identify functional SP22 fragments also lend themselves to testing in random peptide phase display technology (Eidne et al., 2000). Briefly, fifteen or twelvemer random peptide phase display libraries can be used to determine what peptides might interact with functional SP22 peptides by competitive displacement of Fab fragments of SP22 antibodies. For this, fixed sperm are allowed to adhere to wells in multiwell plates, and immunostaining for SP22 is evaluated in the absence and presence of unique and random peptides expressed by the phage library. Once the competitive peptides are identified by amino acid sequence analysis, increased amounts of peptide can be synthesized and used as alternative molecular antagonists to antibodies directed against functional fragments.

Another alternative is to screen thousands of small molecule organics for their ability to competitively display Fab fragments to functional SP22 fragments.

Screening with SP22 Antibody

It is apparent from the above description of SP22 antibodies that a wide variety of diagnostic tests is possible using the antibodies of the invention. In attempting to diagnose causes of infertility, an immunoassay to detect decreased levels of SP22 on sperm is a useful adjunct to known hormone assay. Further uses of the antibodies include testing livestock for candidates for artificial insemination: the higher the levels of SP22 in the potential donor, the more likely artificial insemination is to be successful. Isolation of SP22 allows production of an antisera containing antibody to SP22 for possible crossreaction with other species, including human SP22. This antibody enables preparation of an enzyme-linked immunosorbent assay (ELISA).

For example, to evaluate antibody binding, polystyrene microwells were precoated with extract of a particular epididymal sperm (rat) or ejaculate (horse, bull, human) sample containing an unknown amount of SP22. Next, SP22 antibody was added, followed by the addition of avidin-bibtin-peroxidase complex. A precipitate formed when a substrate such as DAB is oxidized by peroxidase in the presence of hydrogen peroxide. A standard curve for SP22 was generated using increasing known amounts of SP22. The amount of SP22 in a sample is then determined by the optical density of the colored precipitate in the sample and the linear regression obtained from the set of SP22 standards.

Aside from ELISA, the amount of SP22 present on the surface of sperm in a sample (epididymal or ejaculate, animal or human) can be determined using quantitative fluorescence spectroscopy or fluorescent light microscopy. For this, sperm are incubated with SP22 antibody and then with labelled Rhodamine or FITC-conjugated second antibody. It is first necessary to determine the relationship between fluorescence of a sample in a fluorometer or a microscopic image, and the optical density of SP22 separated by two dimensional gel electrophoresis. Once this is established, fluorescence can be related to fertility.

It is also important to determine the relationship between the number of sperm is a sample which express (SP22) (i.e., fluoresce), the degree of the expression or fluorescence, and fertility. This is particularly true for men considering assisted reproductive technologies. For example, if only a critical number (X) of sperm is needed to express a threshold amount (Y) of SP22 for a successful attempt at fertility, it is possible to selectively remove those sperm not expressing SP22 in the ejaculate and use only those sperm that do express a sufficient amount of SP22, for assisted reproductive technologies such as intra uterine transfer or IVF following dissociation of SP22 expressing sperm from the SP22 antibody.

To determine if there is a relationship between the number of sperm expressing SP22 and the extent to which they express it, sperm binding SP22 antibody or antagonist are evaluated by quantitative indirect fluorescence microscopy. For this, Rhodamine or FITC immunolabeling is performed on an aliquot of sperm equivalent to that used for in utero insemination, and the number of sperm that fluoresce is determined along with the relative degree of fluorescence of individual sperm in a sample. The resulting fluorescence histograms are related to fertility assessed by artificial (in utero) insemination. To determine whether a critical number of SP22 expressing sperm are requisite to fertility, an aliquot equivalent to that used for in utero insemination is subjected to immunoabsorption. Polystyrene microwells are precoated with SP22 antibody and sperm in the ejaculate are allowed to bind. Those sperm not binding are washed away, antibody-bound sperm are recovered following dissociation of the antibody with incubation in 0.1 M lithium diiodosalicylate, and increasing numbers of these SP-22 expressing sperm are inseminated in utero.

Conservative amino acid substitutions according to the present invention, e.g., as presented above, are known in the art and would be expected to maintain the biological and structural properties of the polypeptide after such amino acid substitutions. Most deletions, insertions, and substitutions according to the present invention are those which do not produce radical changes in the characteristics of the protein or peptide molecules. One skilled in the art will appreciate that the effect of substitution can be evaluated by routine screening assays, either immunoassays or bioassays. For example, a mutant typically is made by site-specific mutagenesis of the peptide molecule-encoding nucleic acid, expression of the mutant nucleic acid in recombinant cell culture, and, optionally, purification from the cell culture, or a biological sample containing SP22, for example, by immunoaffinity chromatography using a specific antibody on a column to absorb the mutant by binding to at least one epitope.

SP22 Amino Acid Sequencing

Cauda epididymal sperm were extract for one hour as described previously (Klinefelter et al., 1997) using 80 mM n-octyl-β-glucopyranoside (OBG) in 10 mM Tris, pH 7.2, to which 0.2 mM phenylmethylsulfonyl fluoride was freshly added. The extract was then concentrated, desalted, and assayed for protein prior to HPLC separation. Fractions highly enriched in SP22 were obtained by reverse phase C4 HPLC using a linear gradient of 20–80% acetonitrile in water with 0.1% TFA. SP22-containing fractions were pooled and aliquots equivalent to 60 μg of protein were loaded for separation on two dimensional 14% SDS-PAGE. Gels were then stained with Coomassie Blue and the SP22 spots punched out and frozen for use in subsequent peptide sequencing. Isolated SP22 protein then was subjected to tryptic digestion, and the resulting peptide mixture was separated by HPLC. Peaks representing homogeneous peptides were selected for sequence determination by Edman degradation, and the resulting peptide sequences were matched against NCBI GenBank protein sequences using the BLAST program.

FIG. 1A shows the SP22 peptides identified by Edman degradation. FIG. 1B shows the full length amino acid sequence of human DJ1. In the Figure, * indicates that one of the threonines (T) in peptide #3 is a Serine (S) in SP22. * indicates that the initial amino acid after the lysine (K) cleavage site, i.e., valine (V), was ambiguous upon sequencing.

Methods

Cauda epididymal sperm were extracted for one hour as described previously (Klinefelter et al., 1997) using 80 mM n-octyl-β-glucopyranoside (OBG) in 10 mM Tris buffer, pH 7.2., to which 0.2 mM phenylmethylsulfonyl fluoride was freshly added. The extract was then concentrated, desalted, and assayed for protein prior to HPLC separation. Fractions highly enriched in SP22 were obtained by reverse phase C4 HPLC using a linear gradient of 20–80% acetonitrile in water with 0.1% TFA. SP22-containing fractions were pooled and aliquots equivalent to 60 μg of protein were loaded for separation by two dimensional 14% SDS-PAGE. Gels were then stained with Coomassie Blue and the SP22 spots punched out and frozen for use in subsequent peptide sequencing. Isolated SP22 protein then was subjected to tryptic digestion and the resulting peptide mixture separated by HPLC. Peaks representing homogeneous peptides were selected for sequence determination by Edman degradation, and the resulting peptide sequences were matched against NCBI GenBank protein sequences using the BLAST program.

Sequencing SP22 cDNA and Northern Blotting

The partial amino acids identified for SP22 were substantially homologous with human DJ-1 (Nagakubo et al., 1997), and a rat testis cDNA library (Stratagene, LaJolla, Calif.) was screened with an EST cDNA (Accession No. AA388672) encoding a mouse DJ-1 homology. A DJ-1 cDNA probe was prepared by random primer labeling with [$^{32}$P]-dCTP (Amersham, Arlington Heights, Ill.) using a Prime-It II kit (Stratagene). Library screening an bacteriophage isolation was carried out using the method of Benton and Davis (1977).

SP22 insert DNA was sequenced using the dideoxynucleotide termination method of Sanger et al., 1977, using the SequiTherm Excel Kit (Epicenter Technologies, Madison, Wis.). Sequence data were assembled using the MacVector analysis package (Oxford Molecular Products, Oxford, England).

To evaluate the tissue specificity of SP22, total RNA was isolated from multiple reproductive and somatic tissues. Northern blotting to 10 μg total RNA was performed as described by Welch et al., 1992, with a stringent wash temperature of 60° C. and an exposure time of 20 hours.

SP22 Peptide Antibody Location

Peptides #1 and #4 (FIG. 1) obtained by Edman degradation were used together as antigen to generate polyclonal antibody. For this, each peptide was synthesized, conjugated to carrier protein, and the two peptide-carrier protein conjugates were used to immunize two four year old female Broder Leicester Merino Sheep (service provided by Chiron Technologies, Raleigh, N.C.). Specifically, each conjugate was emulsified in 1 ml of Freund's complete adjuvant (approx. 0.3 mg each peptide) followed by intramiuscular injection. Similar injections were administered two and six weeks later using Freund's incomplete adjuvant. Serum was collected two weeks after the final injection.

Peptides #1 and #4 (2 mg each) were also coupled to CNBr-activated Sepharose and used for affinity purification of anti-SP22 peptide IgG. Briefly, 10 ml of immune serum were mixed with 1 ml peptide-linked Thiopropyl-Sepharose 6B overnight at 4° C. Bound anti-SP22 peptide IgG was eluted with 0.1 M glycine-HCl, pH 2.5. IgG was subsequently neutralized, desalted, concentrated, and assayed.

Affinity-purified anti-SP22 peptide IgG (2 mg/ml) was used to localize SP22 in both two dimensional gels and on sperm. For immunoblotting, proteins in sperm extracts were first resolved by mini-two dimensional gel electrophoresis, and subsequently transferred onto PVDF membranes. The blotted membranes were incubated for one hour at 34° C. in DPBS with 1% BSA containing 10% normal rabbit serum. Next, affinity purified anti-SP22 peptide IgG (1:1000) was added and blots were allowed to shake overnight at 4° C. Biotinylated rabbit anti-sheep IgG and ABC reagents were added as per Vectastain instructions and the peroxides reaction product was visualized using the VIP substrate kit. To control for nonspecific binding, pre-immune serum was used in place of the affinity-purified anti-SP22 peptide IgG.

For immunocytochemistry, cauda epididymal (rat) or ejaculated sperm (bull, human) were washed twice with DPBS and either fixed in Zamboni's fixative containing 0.1% Triton X-100 for one hour at 4° C. or incubated directly in blocking buffer (DPBS containing 1% BSA and 10% normal rabbit serum) for one hour at 34° C. Fixed sperm were incubated in blocking buffer after fixation. Blocking buffer was removed after centrifugation and 10×10$^6$ sperm were incubated in 1 ml of Dulbecco's Phosphate Buffered Saline (DPBS) containing 20 µg of affinity-purified anti-SP22 peptide IgG (1:100) for one hour. After washing, FITC-labeled rabbit anti-sheep IgG (1:25) was added for one hour. Sperm were washed again and mounted using anti-fade mounting medium. The specificity of immunostaining was verified by adding a 20 µg mixture of peptides #1 and #4 (10 µg each) in conjunction with the affinity-purified anti-SP22 IgG.

Modulation of Fertility with SP22 Peptide Antibody

Artificial (in utero) insemination in the rat was conducted as previously described (Klinefelter et al., 1997). Briefly, 10×10$^6$ cauda epididymal sperm were incubated for five minutes at 34° C. either with or without 10 µl of the affinity-purified anti-SP22 IgG (1:50), and 5×10$^6$ were injected into each uterine horn of LHRH-synchronized, cervically-stimulated adult females while under halothane anesthesia. Nine days later, the inseminated females were sacrificed and the number of implants and corpora lutea were enumerated. Fertility was expressed as the number of implants relative to the number of corpora lutea.

Quantification of SP22 to Detect Alterations in Fertility Due to Testicular Toxicants Bromochloroacetic acid (BCA), a naturally-occurring by-product of drinking water disinfection, was administered to adult male rats in water by gavage in graded doses, i.e., 0, 8, 24, and 72 mg/kg body weight. The rats were dosed daily for fourteen days. On day fifteen, sperm from the proximal cauda epididymis were prepared for artificial insemination as described above. The sperm remaining after insemination were washed and extracted with 80 mM n-octyl-β-glucopyranoside (OBG) in 10 mM Tris, pH 7.2. The extract was then concentrated, desalted, and protein concentration was determined prior to separation on 14% mini, two-dimensional SDS-PAGE gels. The silver-stained SP22 protein was background corrected and the integrated optical density was correlated with the fertility of these sperm.

SP22 Amino Acid Sequencing

Figures 2, 8:
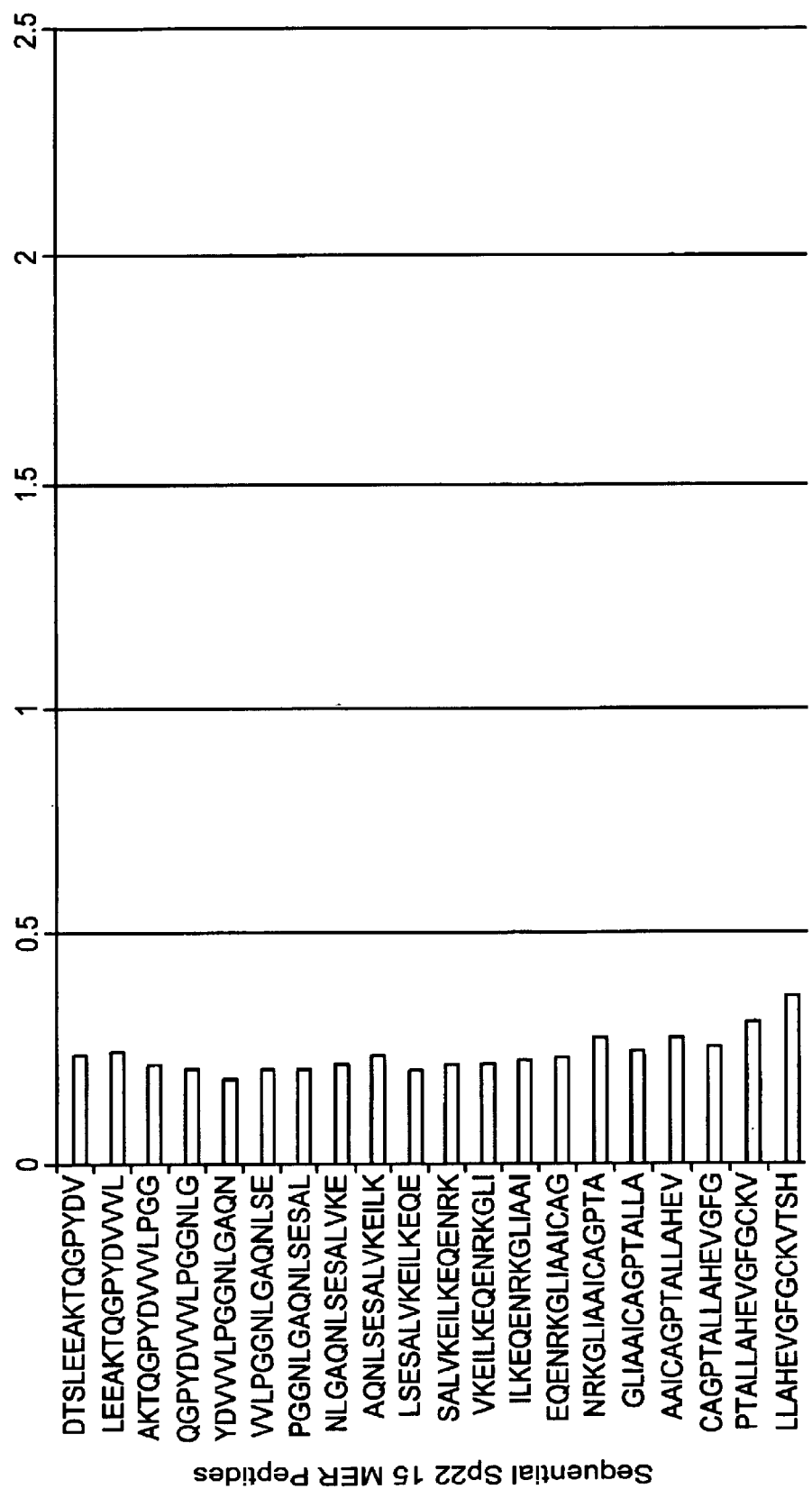
FIG. 2 shows SEQ ID NO:3 which compares the nucleotide and amino acid sequences of the two SP22 mRNA transcripts, A and B. The A transcript is SP22A and is unique to the testis and referred to as SEQ ID NO:2.
FIG. 8 is a plot illustrating the immunoreactivity of overlapping 15 mer SP22 peptides with affinity-purified anti-SP22 peptide Ig. Antiserum was affinity-purified and diluted 1:100 prior to use. The two reactive peaks within the 189 amino acid SP22 sequence are: Peptide A (TVAGLAGKDPVQCSR) and Peptide B (DGLILTSR).
Figures 3, 8:
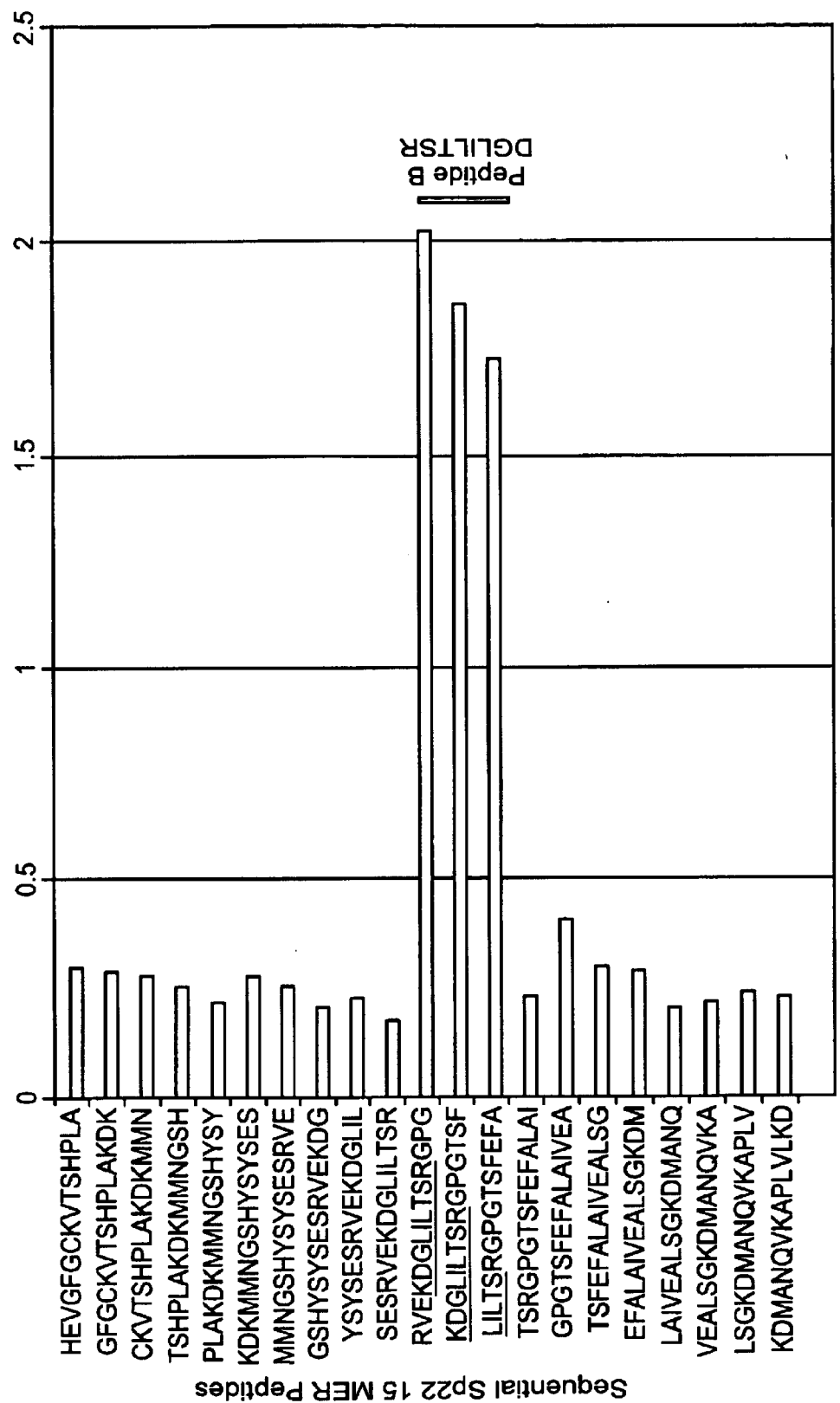

Four peptides were obtained as shown in FIG. 1. Each peptide was relatively short in length and each was flanked by trypsin cleavage sites at Lys (K) or Arg (R). Peptides #1, 2, and 4 matched sequences in the DJ-1 protein recently described in human Hela cells (Nagakubo et al., 1997). Moreover, five of the seven amino acids contained within peptide #3 following Edman degradation matched the DJ-1 sequence. Of the two amino acids in peptide #3 which did not match DJ-1 sequence, one is now known to be erroneous (i.e., G should be H), and the other represents a T (human DJ-1) to S (rat SP22) substitution in the DNA sequence (FIG. 2). Comparisons of human DJ-1 with expressed sequence tagged cloned from mouse indicated that these peptides were also perfectly conserved between human and mouse.

FIG. 1 shows the SP22 peptides identified by Edman degradation and the full length amino acid sequence of SP22 and the corresponding homology to human DJ-1.

Cloning and Sequencing SP22 cDNA

Sequencing of SP22 cDNAs obtained from a rat testis cDNA library indicated that SP22 was encoded by two distinct mRNA sequences with divergent 5' sequences (FIG. 2).

Of the four peptides derived from direct peptide sequencing of purified SP22, FIG. 1, peptides #1, 2 and 4 were found to match the predicted SP22 amino acid sequence exactly. Peptide #3 was found to contain a single discrepancy where glycine was predicted rather than histidine. The 3' untranslated region of the SP22 cDNAs contained a typical polyadenylation signal (AATAAA), although separate sites of polyadenylation were observed. Database searches using the SP22 sequence indicated a substantial homology (91% identity) with the human DJ-1 protein (FIG. 1) and suggest that SP22 and DJ-1 are members of the same protein family. All matching with DJ-1 was confined to the 189 amino acid residues common to the three SP22 transcripts.

FIG. 2 demonstrates that SP22 is encoded by alternatively-spliced mRNAs. The divergent 5' ends of three SP22 cDNAs designated A (plain text) and B (italics). Peptide sequencing matched perfectly with the exception of peptide #3, where a histidine (H*) was observed in place of glycine (G). The canonical polyadenylation signal (AATAAA) is underlined. Observed multiple polyadenylation sites are indicated by asterisks.

FIG. 1 illustrates the substantial homology of rat SP22 with human DJ-1 protein. The 189 amino acids of SP22 conserved between all SP22 sequences (upper) are compared with the complete DJ-1 sequence (lower). Sequence identities are indicated by solid bars, conservative substitutions are shown by a colon, and divergent residues are indicated by gaps. All peptide sequences are identical between SP22 and DJ-1 with the exception of peptide #3, where the observed threonine (T) to serine (S) change was observed both in the directed and predicted amino acid sequences. The high degree of identity suggests that SP22 and DJ-1 belong to the same family of proteins.

FIG. 3, shows that Northern blotting of total RNA from rat testis (T), epididymis (E), brain (B), liver (L), and kidney (K) revealed the presence of a 1.0 kb mRNA in all tissues. However, a 1.5 kb transcript also appeared in the testis lane, indicating the presence of the testis-specific SP22A mRNA (SEQ ID NO: 2).

Peptide Antibody Localization

Figure 4:
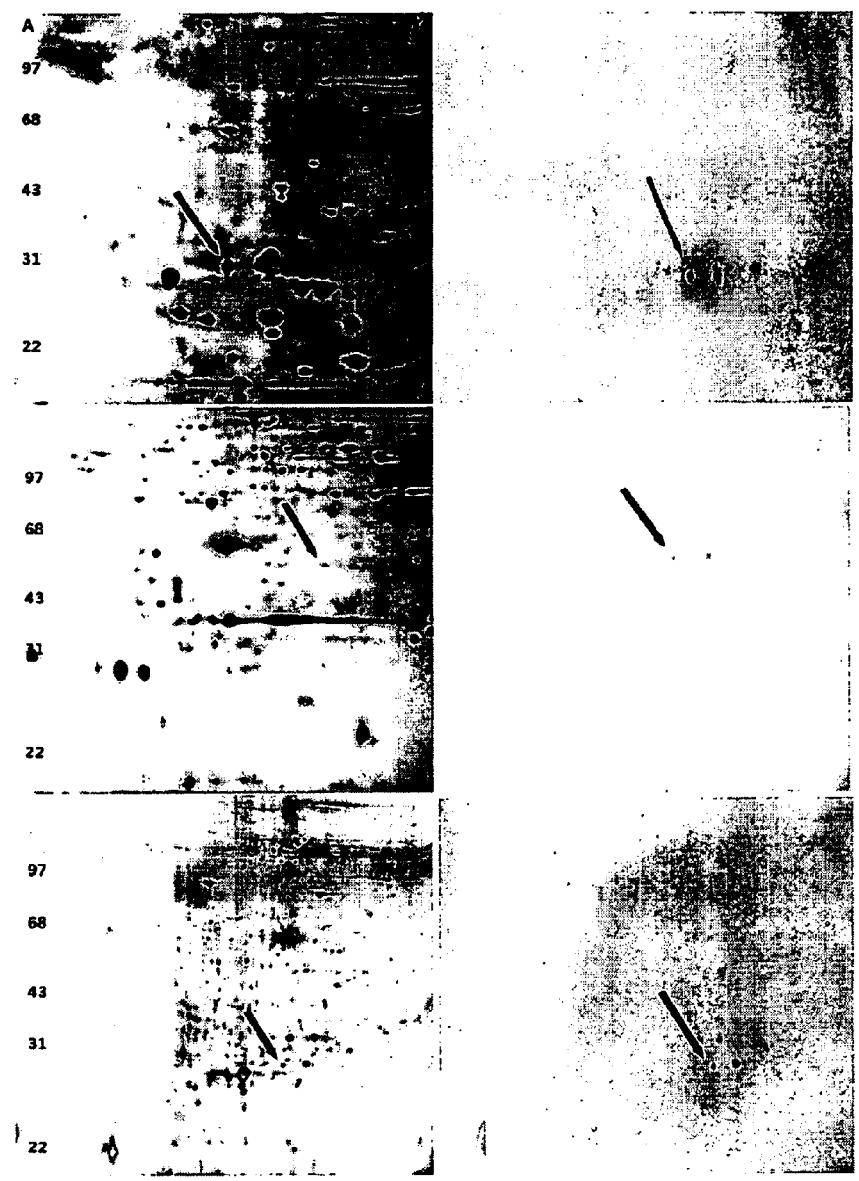
FIG. 4 shows silver stained two dimensional gels and corresponding immunoblots showing localization of SP22 using anti-SP22 peptide Ig in rat cauda epididymal sperm extract (top), rat cauda sperm membrane preparation (middle), and rat rete testis sperm extract (bottom).
Figure 5:
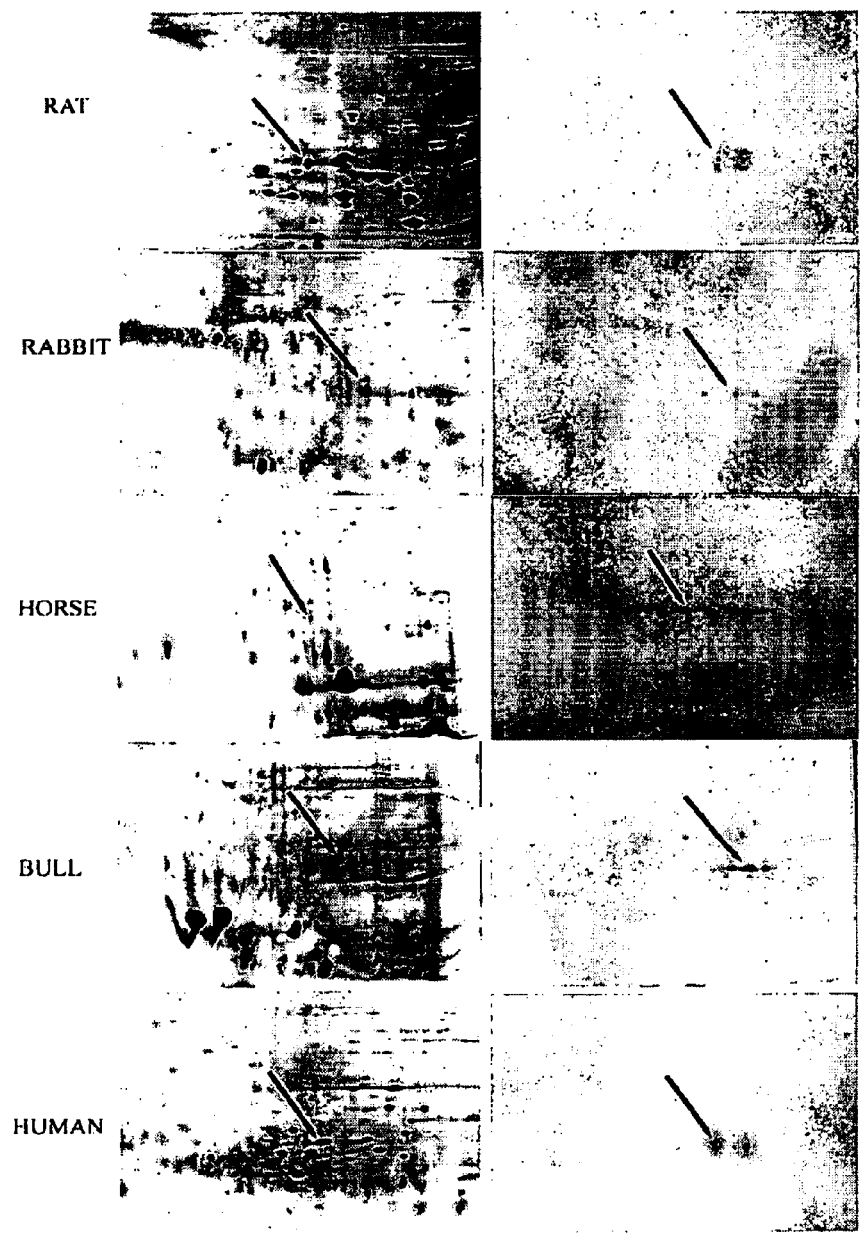
FIG. 5 shows silver stained two dimensional gels and corresponding immunoblots showing localization of SP22 using anti-SP22 peptide Ig in detergent extracts of sperm from various species.

Affinity-purified anti-SP22 peptide IgG recognized SP22 in the detergent extract of cauda epididymal sperm, solubilized membranes isolated from cauda epididymal sperm, and a detergent extract of sperm recovered from the rat testis 18 hours after efferent duct ligation (FIG. 4). No signal was detected on blots incubated with preimmune serum. The fact that a slightly more basic protein at the same apparent molecular weight was also recognized by the affinity-purified anti-SP22 peptide IgG suggests that post-translationally modified variants of SP22 exist. When affinity-purified anti-SP22 peptide IgG was used to probe immunoblots of detergent extracts of bull, rabbit, stallion, and human sperm, a pattern of immunorecognition identical to that seen for the rat was evident (FIG. 5), suggesting that SP22 and its isoform(s) are present in the sperm membrane regardless of species.

Figure 9:
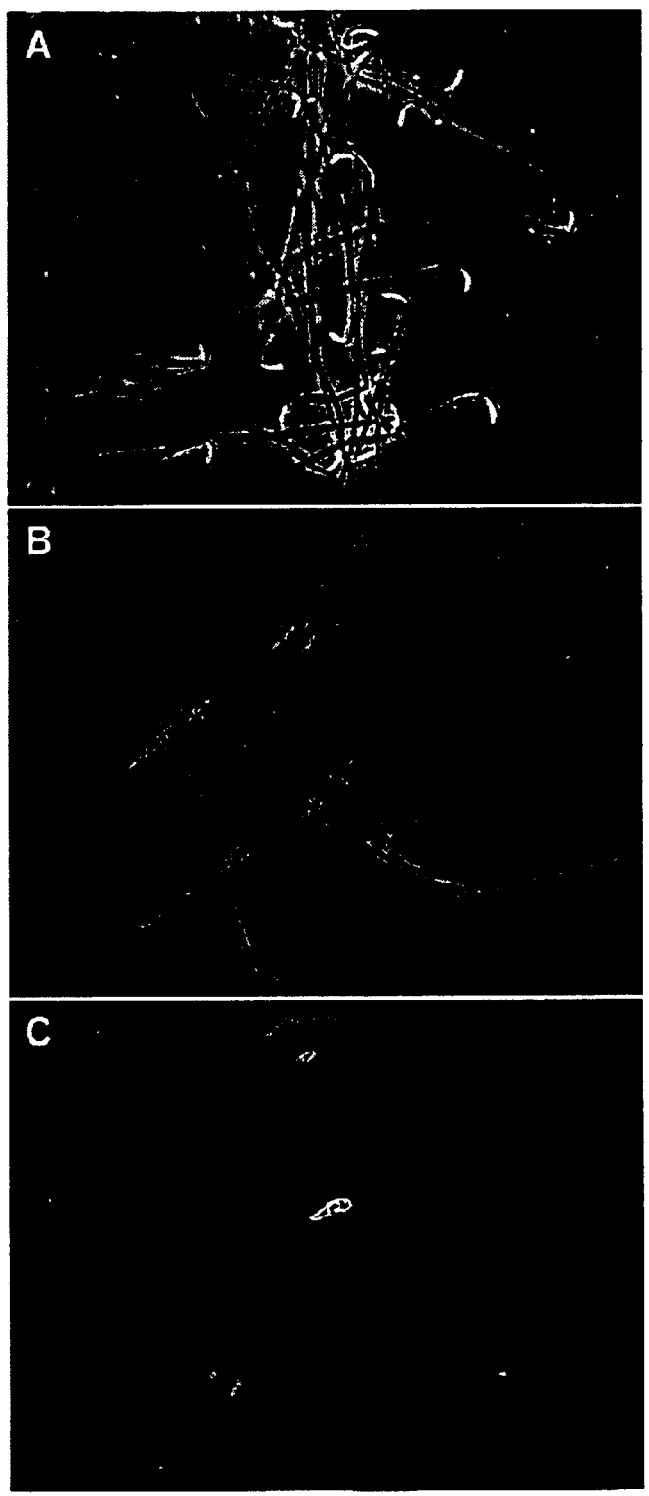
FIGS. 9A–9C are micrographs depicting (A) immunostaining over the equatorial segment of the head of fresh, unfixed cauda epididymal rat sperm using affinity-purified anti-SP22 peptide Ig; (B) This immunostaining is completely ablated by coincubation with 20 micrograms (10 micrograms each) of a mixture of the 15 mer and 8 mer peptides used as immunogen; (C) Immunostaining over the head of human sperm with the anti-SP22 peptide Ig; staining is restricted to the equatorial segment using anti-recombinant SP22 Ig.

Affinity-purified anti-SP22 peptide Ig localized over the anterior ventral, i.e., equatorial, region of the head on either fixed or fresh, unfixed cauda epididymal rat sperm (FIG. 9). Immunostaining was completely ablated by coincubating the Ig with a mixture of the immunogenic SP22 peptides, i.e., peptides #1 and #4 (equivalent to peptides A and B from mimotope analyses). When peptides #1 and #4 were tested separately during coincubation with the anti-peptide Ig, the results indicated that only peptide #1 was exposed on fresh sperm. Coincubation with peptide #1 ablated all immunostaining, while coincubation with peptide #4 did not influence the level of immunostaining (FIG. 10). Staining was also evident over the head of human sperm (FIG. 9). Using the affinity-purified anti-recombinant SP22 Ig, this staining was restricted to the equatorial segment of sperm from all species examined, including human.

Modulation of Fertility with SP22 Peptide Antibody

Figure 11:
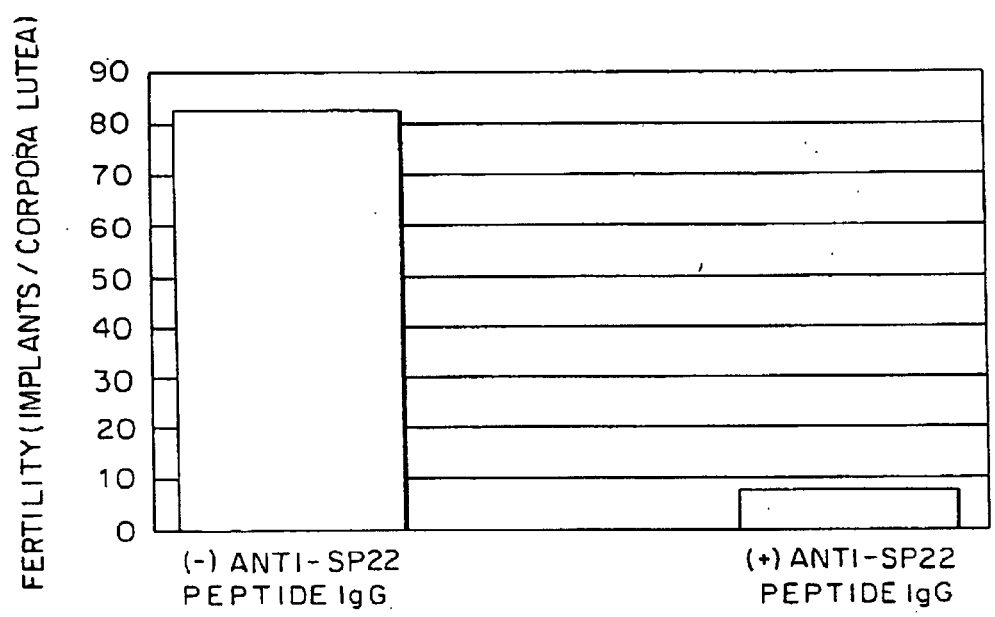
FIG. 11 is a graph of fertility data using affinity-purified anti-SP22 peptide Ig. When rat cauda epididymal sperm were inseminated without pre-incubation with Ig, fertility as expressed as the number of fetal implants relative to the number of corpora lutea on day 9 of gestation averaged 83%. In contrast, when sperm were incubated for five minutes with 10 microliters of affinity purified anti-SP22 peptide Ig (1:50) prior to insemination in utero, fertility was decreased significantly to only 7%. Indeed, only one of six females had any implants at all.

When cauda epididymal sperm were incubated for five minutes with anti-SP22 peptide antibody (1:50) just prior to insemination into the uterine horns of receptive females, fertility was significantly reduced (FIG. 11). Indeed, while fertility of sperm that was not incubated with antibody averaged 83% (ranging from 64 to 100%), only one of the six females inseminated with sperm that were incubated with antibody had any implants. The fertility of this one female was below normal (44%).

To repeat and extend these results, affinity-purified anti-peptide Ig (10 microliters, equivalent to 20 micrograms Ig) was incubated 1:50 (0.04 microgram/microliter) with cauda epididymal sperm five minutes prior to insemination. Fertility was once again reduced to less than 10% (FIG. 12). In contrast thereto, when 20 micrograms of peptide #1, equivalent to Peptide A from mimotope analysis, was added to the Ig and sperm for five minutes prior to insemination, the resultant fertility was equivalent to historical control values. However, when 20 micrograms of peptide #4, equivalent to Peptide B from mimotope analysis, was added to the Ig and sperm for five minutes prior to insemination, the reduction in fertility was as significant as when sperm were incubated with Ig alone. These data clearly demonstrate that the SP22 fragment peptide #1 (i.e., Peptide A from mimotope analysis) is a functional fragment in the modulation of fertility.

Correlation of SP22 with Infertility Induced by a Testicular Toxicant

To date, four epididymal toxicants and two testicular toxicants have been evaluated with respect to their ability to compromise both SP22 expression on sperm and the fertility of these sperm. If is clear from FIG. 6 that the relationship between SP22 levels and fertility is similar, i.e., non-linear and threshold-like, and the correlation between these endpoints is quite high. From a diagnostic perspective these data are meaningful only if both the overall correlation and predictability values are good. FIG. 7 represents all data from the 131 animals studied to date following either testicular or epididymal insults. It is clear that the correlation remains quite high ($r^2=0.78$), but more importantly, the predictive value of SP22 can be evaluated as follows:

(1) establish a threshold value for the background-corrected, integrated optimal density of SP22 based on the point on the predicted line with the smallest 95% confidence interval (i.e., the least error); the threshold value for SP22 is 3594 at this point; and (2) Establish a threshold for fertility at the lower 95% confidence interval at this point; the value for fertility is 43% at this point.

Using these criteria, the true positive rate is 94% and the false positive rate is only 3.8%.

Production of Full Length Recombinant SP22 (rSP22), Antibody to rSP22, and Modulation of Fertility with rSP22 Ig A recombinant SP22 expression cassette encoding the entire SP22 protein was synthesized by PCR amplification of the coding region from the SP22 cDNA. This cassette was cloned into a pQE8 plasmic containing a prokaryotic lac promoter region and the Shine-Delgado ribosome binding site to facilitate expression in E. coli. The plasmid also contained a sequence encoding a series of six histine residues (6×His) to allow rapid purification of the recombinant protein. Once transfected into E. coli, SP22 production was induced by the addition of isopropyl-thio-β-D-galactopyranoside (IPTG) to activate the lac promoter. The 6×His tag has a pH-dependent high affinity for nickel and is capable of binding in the presence of high concentration of urea and guanidinium salts. After growth in culture for 5–6 hours, cells were harvested by centrifugation and solubilized in 6M guanidine hydrochloride, 100 mM phosphate at pH 8.0. The nickel agarose column was washed stepwise in 8M urea, 100 mM phosphate butter at pH 8.0, pH 6.3, pH 5.9, NS DINlly pH 4.5. The bacterial proteins were either not retained on the column or were eluted in the first three washes, while recombinant SP22 (rSP22) was eluted at pH 4.5. The purified rSP22 yields for one liter of bacterial culture were in the milligram range.

Purified rSP22 was used unconjugated as antigen to immunize two four year old Border Leicester Merino sheep (service provided by Chrion Mimotopes, Clayton Victoria, Australia). Briefly, 1 mg of rSP22 was resuspended in 1 ml of phosphate buffered saline and emulsified with an equal volume of Complete Freund's Adjuvant and approximately 1 ml (half of the total volume) was injected into each sheep intramuscularly. A second and third immunization followed two and three weeks later, using Incomplete Freund's Adjuvant. Sera were tested by ELISA for rSP22-specific antibody titre. Sera exhibited high titre based on ELISA and anti-rSP22 Ig was purified by affinity chromatography on a Sepharose column conjugated with 25 mg of rSP22. Anti-rSP22 Ig was tested for ability to inhibit fertility both in vivo and in vitro. For in utero inseminations, 10 microliters (equivalent to 60 micrograms) was incubated 1:50 with rat cauda epididymal sperm, and sperm were allowed to incubate five minutes prior to insemination. For in vitro fertilization, a similar Ig concentration was incubated with cauda epididymal sperm in the presence of eggs overnight. Fertility was assessed in vivo on day 9 of gestation by the number of fetal implants relative to the number of corpora lutea. Fertilization was assessed in vitro by the percentage of eggs containing a sperm tail the next morning. In addition the relative number of sperm binding to the zona after insemination was evaluated.

Antibodies and Other Molecular Antagonists to SP22

Antibodies to SP22 can be prepared by conventional polyclonal or monoclonal technologies. These antibodies can be raised in rabbits, mice, sheep, or tissue culture cells derived therefrom, or can be products of cells of human origin.

To prepare the antibodies, purified native SP22, SP22 peptides (i.e., fragments), or recombinant SP22 (full length or functional fragments) may be used to effectively immunize animals. These antibodies may be generated either in host animals or in recipients in vivo (i.e., via vaccine formulation). It should be noted that with respect to vaccine generation, functional fragments specific to the native molecule should be selected. Moreover, antibodies to multiple functional fragments may be generated to enhance inhibition of fertility. Antibodies generated in host animals may be administered by periodic injections (male or female), or by vaginal delivery upon emulsification in appropriate stabilizer/carrier. Similarly, peptide ligands shown to competitively inhibit binding of antibodies to functional SP22 fragments (e.g., a peptide ligand for Peptide A) would be expected to effectively inhibit fertility. Again, such ligands, emulsified in similar delivery systems, could be administered singularly or in combination until maximum inhibition was achieved.

Antibodies to SP22

Antibodies to SP22 can be prepared by any conventional means, and they can be either polyclonal or monoclonal. They may be raised in rabbits, mice, or other animals or tissue culture cells derived therefrom, or can be products or cells of human origin. They may also be produced by recombinant DNA technology either in a form identical to that of the native antibody or as chimeric molecules, constructed by recombination of antibody molecules of human or animal origin or in other forms chosen to make the antibodies most suitable for use in therapy.

For preparation of the antibodies, either purified SP22 or a peptide identical to the known sequences of fragments thereof, e.g., to the N-terminal protein sequence, may be used to immunize animals. A further possibility is to fuse one of the nucleotide sequences coding an active fragment of SP22 to the gene coding for protein A, to express the antibody. The antibody is then purified by affinity chromatography on a Sepharose column and used to immunize animals.

Preparation of Antibodies to SP22

Antibodies (both polyclonal and monoclonal) to SP22 may be prepared for diagnostic and therapeutic uses, including but not limited to fertility control (contraception) and fertility assessment (screening).

"Antibody" in this context refers to a synthetic protein which binds SP22 and negates its biological function. Antibodies to SP22 are prepared by either polyclonal or monoclonal techniques:

A. Polyclonal Antibody Production

For polyclonal antibody production, adult sheep, mice or rabbits are immunized with 25 or 100 mg of SP22 suspended in Freund's complete adjuvant. This preparation is injected subcutaneously and is followed by booster injections of SP22 mixed with incomplete adjuvant. Sera obtained after the final booster injection are checked for titer, affinity, and specificity.

Specifically, for rabbits, 100 micrograms of SP22 protein as obtained above, or peptides which are analogs of SP22, were solubilized in 0.5 mL physiological saline and emulsified with an equal volume of Freund's adjuvant to prepare inoculum sites in the back. Two New Zealand White female rabbits, weight 2.5–3.5 kg, were bled via the marginal ear vein for pre-immune serum. Approximately 50 microliters of inoculum was injected into 20 sites within the shaved area. The rabbits were boosted in similar fashion four weeks later. Two weeks later, the rabbits were bled again via the marginal ear vein, and sera containing the polyclonal antibodies was obtained.

To produce antiserum to SP22, a detergent extract of cauda epididymal sperm was chromatographed by reverse-phase HPLC and fractions enriched in SP22 were run in analytical two dimensional gels. Coomassie-stained SP22 punches were subsequently subjected to electroelution and electroeluted material was desalted, concentrated, and assayed for protein. After verifying that the electroeluted material was SP22, 25 micrograms were mixed with Freund's complete adjuvant and injected subcutaneously into each of six mice. Four other mice received only adjuvant.

After four weeks, each mouse was boosted with 12.5 micrograms of SP22 mixed with Freund's incomplete adjuvant. After another ten days, a final similar booster was given. The mice were euthanized the days after the final booster, and the serum was collected.

B. Monoclonal Antibody Production

BALB/c mice were immunized initially via i.p. injections with 50 ug of full length recombinant SP22 and later boosted similarly with native SP22. Services were provided by BioCon, Inc. (Rockville, Md.). Spleens were collected and cell suspensions were prepared by perfusion with DMEM. The BLAB/c spleen cells were fused with SP 2/)-Ag 14 mouse myeloma cells by PEG and the resultant hybridomas grown in HAT selected tissue culture media plus 20% fetal calf serum. The surviving cells were allowed to grow to confluence. The spent culture medium was checked for antibody titer, specificity, and affinity.

Specifically, the mice were immunized with SP22 adjuvant emulsion described above. Each mouse first received 0.2 mL of this emulsion intraperitoneally, and then was reinfected in similar fashion with 0.1 mL six weeks later. Mouse serum was obtained then days after the second injection and then tested for anti-FRP activity via ELISA. The mouse exhibiting the highest possible anti-FRP activity was chosen for cell fusion.

Spleen cell suspension containing B-lymphocytes and macrophages was prepared by perfusion of the spleen. The cell suspension was washed and collected by centrifugation; Myeloma cells were also washed in this manner. Live cells were counted and the cells placed into a 37° C. water bath. One mL of 50% polyethylene glycol in DMEM was added slowly. The cells were incubated in the PEG for one to 1.5 minutes at 37° C., after which the PEG was diluted by the slow addition of media. The cells were pelleted and 35 to 40 mL of DMEM containing 10% fetal bovine serum is added. The cells were then dispensed into tissue culture plates and incubated overnight in a 37° C., 5% $CO_2$, humidified incubator.

The next day, DMEM-FCS containing hypoxanthine, thymidine, and aminopterin (HAT medium) was added to each well. The concentration of HAT in the medium to be added was twice the final concentration required, i.e., $H_{final} = 1 \times 10^{-4} M$ $A_{final} = 4 \times 10^{-7} M$, and $T_{final} = 1.6 \times 10^{-5} M$.

Subsequently, the plates were incubated with HAT medium every three to four days for two weeks. Fused cells were thereafter grown in DMEM-FCS containing hypoxanthine and thymidine. As cell growth became ½ to ¾ confluent on the bottom of the wells, supernatant tissue culture fluid was taken and tested for SP22 specific antibody by ELISA. Positive wells were cloned by limiting dilution over macrophage or thymocyte feeder plates, and cultured in DMEM-FCS. Cloned wells were tested and recloned three times before a statistically significant monoclonal antibody was obtained. Spent culture media from the chosen clone contained antibody which bonds SP22 in all dilutions tested.

C. Antibody to SP22 Peptides

SP22 is identified by its biological functions and activities set forth herein, as well as by it size of approximately 22 kD and isoelectric point of 5.25. However, changes in form and the substitution of fragments or equivalents are contemplated as circumstances may suggest or render expedient, including variations in methods for physically characterizing the protein. For instance, it may be necessary to generate polyclonal antibodies to peptide fragments of SP22 if sufficient amounts of purified SP22 cannot be obtained relatively easily.

In addition to the antibodies which are identical to the naturally-occurring SP22 peptide antibody, the present invention embraces epitopes which are substantially homologous with such antibodies.

The term "antibody" is meant to include polyclonal antibodies, monoclonal antibodies, chimeric antibodies, anti-idiotypic antibodies to antibodies that can be labeled in soluble or bound form, as well as active fractions thereof provided by any known technique, such as, but not limited to, enzymatic cleavage, peptide synthesis, and recombinant techniques.

Polyclonal antibodies are heterogeneous populations of antibody molecules derived from the sera of animals immunized with an antigen. A monoclonal antibody contains a substantially homogeneous population of antibodies specific to antigens, which population consists substantially similar epitope binding areas.

Chimeric antibodies are molecules in which different proteins are derived from different animal species, such as those having the variable region derived from a murine monoclonal antibody and a human immunoglobulin constant region. Chimeric antibodies are primarily used to reduce immunogenicity in application and to increase yields in production, for example, where murine monoclonal antibodies have high yields from hybridomas but higher immunogenicity in human, such that human murine chimeric monoclonal antibodies are used.

Chimeric antibodies and methods for their production are known in the art [Cabilly et al., *Proc. Natl. Acad. Sci. USA* 81:6851–6855 (1994); Boulilanne et al., *Nature* 312:643–646 (1984); European Patent Application 125023; Neiberger et al., *Nature* 314:2680279 (1985); Taniguchi et al., European Patent Application 171496; Morrison et al., European Patent Application 173494; Neuberger et al., PCT Patent Application WO 8601533; Kudo et al., European Patent Application 184187; Sahagah et al., *J. Immunol.* 137:1066–1074; Robinson et al., PCT Patent Application WO 8702671; Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane, *Antibodies, a Laboratory Manual*]. Each of these references is hereby incorporated herein by reference in its entirety.

An anti-idiotypic antibody is an antibody which recognizes unique determinants generally associated with the antigen-binding site of an antibody. An anti-idiotypic antibody can be prepared by immunizing an animal of the same species and genetic type (e.g., a mouse strain) as the source of the monoclonal antibody with the monoclonal antibody to which an anti-idiotypic antibody is being prepared. The immunized animal will recognize and respond to the idiotypic determinants of the immunizing antibody by producing an antibody to these idiotypic determinants, i.e., the anti-idiotypic activity. See, for example, U.S. Pat. No. 4,669,880, the entire contents of which are hereby incorporated by reference.

The anti-idiotypic antibody may also be used as an immunogen to produce an immune response in yet another animal, producing a so-called anti-anti-idiotypic antibody. The anti-anti-idiotypic antibody may be epitopically identical to the original monoclonal antibody which induces the anti-idiotypic antibody. Thus, by using antibodies to the idiotypic determinants of a monoclonal antibody, it is possible to identify other clones expressing antibodies of identical specificity.

Accordingly, monoclonal antibodies generated against SP22, and related proteins of the present invention, may be used to induce anti-idiotypic antibodies in suitable animals, such as BALB/c mice. Spleen cells from such immunized mice are used to produce anti-idiotypic hybridomas secreting anti-idiotypic monoclonal antibodies. Further, the anti-idiotypic monoclonal antibodies can be coupled to a carrier such as keyhole limpet hemocyanin (KLH) and used to immunize additional BALB/c mice. Sera from these mice will contain anti-anti-idiotypic antibodies that have the binding properties of the original monoclonal antibodies specific for SP22 or epitopes thereof.

The term "antibody" is also meant to include both intact molecules as well as active fractions thereof, such as, for example, those which are capable of binding antigen. Fab and F(ab')2 fragments lack the Fc fragment of intact antibody, clear more rapidly from the circulation, and may have less non-specific tissue binding than an intact antibody, cf. Wahl et al., *J. Nucl. Med.* 24:316–325, 1983.

The term "antagonist" includes antibody, complementary peptides or fragments thereof, or other small molecules which inhibit the activity of the protein.

The term "substantially homologous", when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

Substantially homologous peptide epitopes may be identified by a variety of techniques. It is known in the art that one may synthesize all possible single substitutions mutants of a known peptide epitope, Geysen et al., *Proc. Nat. Acad. Sci. (USA)* 18:3998–4002, 1984. While the effects of different substitutions are not always additive, it is reasonable to expect that two favorable or neutral single substitutions at different residue positions in the epitope can safely be combined in most cases.

One may also synthesize a family of related single or multiple substation mutants, present the mixture to a cell line capable of presenting the desired epitopes, and expose the cells to suitable restricted antigens. If the cells are lysed, effective epitopes may be identified either by direct recovery from the cells or by a progressive process of testing subsets of the effective peptide mixtures. Methods for the preparation of degenerate peptides are described in Rutter, U.S. Pat. No. 5,010,175; Haughter et al., *Proc. Nat. Acad. Sci. (USA)* 82:5131–5135 (1985); Geysen et al., op. cit.; WO86/06487; and WO86/00991.

In devising a multiple mutagenesis strategy, a person of ordinary skill would of course give weight to the single substitution mutant data in determining both which residues to vary and which amino acids or classes of amino acids are suitable replacements.

It is also possible to predict substantially homologous epitopes by taking into account studies of sequence variations in families or naturally occurring homologous proteins Certain amino acid substitutions are more often tolerated than others, and these are often correlated with similarities in size, charge, etc., between the original amino acid and its replacement. Insertions or deletions of amino acids may also be made, as described above.

Clones

Once an antibody to, or portions sequence of, SP22 is available, it will be necessary to screen cDNA libraries to identify the cDNA clones that produce SP22. SP22 may be produced by methods other than recovery from male animals. In particular, a cDNA probe is prepared against a partial sequence of SP22 and used to identify the SP22 genome in cells from any mammalian species. The identified genome is then inserted into a plasmid which is then employed to produce recombinant SP22 in proliferating bacteria or other hosts according to methods known in the art. This will be useful in the methodologies, e.g., immunocontraception, addition to sperm, described herein. However, not only will these utilities require large amounts of SP22, they will also require large quantities of the SP22 antibody. This is accomplished in batch hybridoma cell culture using proven methods. The same processes can be used to identify antagonists to SP22 and fragments and derivatives thereof.

Contraception

Antibodies to SP22 can be used for contraception as well as for assaying fertility. A reversible contraceptive vaccine is provided by administering to an animal subject SP22 as described above in an amount effective to reduce the fertility of that subject via generation of antibodies to SP22. Partial reduction in fertility, i.e., effects which are reflected as a reduction in fertility in a population of subjects, are intended as within the scope of the present invention.

Any animal which expresses sperm surface SP22 may be treated by the immunocontraceptive method of the present invention, including both birds and mammals. Exemplary mammals include mice, rabbits, dogs, cats, cows, pigs, sheep, horses, and humans. Mammalian subjects are preferred. The vaccine can be administered to either females or males by any suitable means, including by intramuscular injection. The antibody can be administered topically, as by vaginal foam or by any convenient topical method in an appropriate carrier, e.g., by nasal spray.

The term "protection", as used herein, is intended to include prevention or suppression of production of fertile sperm.

It will be understood that in medicine, it is not always possible to distinguish between preventing and suppressing, since the ultimate inductive event or events may be unknown, latent, or the patient is not ascertained until well after the occurrence of the event of events. The term "protection", as used herein, is meant to include prophylaxis.

The form of administration may be systemic or topical. For example, administration of such a composition may be by various parenteral routes such as subcutaneous, intravenous, intradermal, intramuscular, intraperitoneal, intranasal, transdermal, vaginal or buccal routes. Alternatively, or concurrently, administration may be by the oral route. Parenteral administration can be by bolus injection or by gradual release over time.

It is understood that the suitable dose of a composition according to the present invention will depend upon the age, health and weight of the recipient. However, the most preferred dosage can be tailored to the individual subject, as is understood and determinable by one skilled in the art, without undue experimentation. This typically involves adjustment of a standard dose, e.g., reduction of the dose if the patient has a low body weight.

Prior to use in humans, a drug is first evaluated for safety and efficacy in laboratory animals. In human clinical trials, one begins with a dose expected to be safe in humans, based on the preclinical data for the drug in question, and on customary doses for analogous drugs, if any. If this dose is effective, the dosage may be decreased to determine the minimum effective dose, if desired. If this dose is ineffective, it will be cautiously increased, with the patients monitored for signs of side effects. See, e.g., Berkow et al., eds. *The Merck Manual*, 15$^{th}$ *edition*, Merck and Co., Rahway, N.J., 1987; Goodman et al., eds., *Goodman and Gilman's The Pharmacological Basis of Therapeutics*, 8$^{th}$ *edition*, Pergamon Press, Inc., Elmsford, N.Y., 1990; *Avery's Drug Treatment: Principles and Practice of Clinical Pharmacology and Therapeutics*, 3$^{rd}$ *edition*, ADIS Press, Ltd., Williams and Wilkins, Baltimore, Md., 1987; Ebadi, *Pharmacology*, Little Brown and Co., Boston, Mass., 1985; which references and references cited therein are entirely incorporated herein by reference.

The appropriate dosage form depends on the composition administered, i.e., the carrier used for the antibody, as well as the mode of administration. Modes of administration include tables, capsules, lozenges, dental pastes, suppositories, inhalants, solutions, ointments, and parenteral depots. See, e.g., Berker, supra, Goodman, supra, Avery, supra, and Ebadi, supra., which are entirely incorporated herein by reference, including all references cited therein.

In addition to the protein or antigen of the invention, a pharmaceutical vaccine composition may contain suitable pharmaceutically acceptable carriers, such as excipients, carriers, and/or auxiliaries which facilitate processing of the active compounds into preparations which can be used pharmaceutically. The amount of antigen administered depends upon factors such as route of administration, species, and the use of booster administration. In general, dose of about 0.1 to about 100 micrograms per kg of body weight may be used. The antigen to SP22 may be prepared at both human and veterinary vaccine formulations. Vaccine formulations of the present invention comprise the antigen in a pharmaceutically acceptable carrier. The antigen is included in the carrier in an amount which is effective to reduce the fertility of the subject being treated. Pharmaceutically acceptable carriers are preferably liquid, particularly aqueous carriers, such as sodium phosphate buffered saline. The vaccine formulations may be stored in a sterile glass container sealed with a rubber stopper through which liquids may be injected and formulations withdrawn by syringe.

Vaccine formulations of the present invention may optionally contain one or more adjuvants. Any suitable adjuvant can be used, such as aluminum hydroxide, aluminum phosphate, plant and animal oils, and the like, with the amount of adjuvant depending on the nature of the particular adjuvant employed. In addition, the vaccine formulations may also contain at least one stabilizer, such as carbohydrates such as sorbitol, mannitol, starch, sucrose, dextrin, and glucose, as well as proteins such as albumin or casein, and buffers such as alkali metal phosphates and the like.

In addition to the active ingredient, i.e., the antigen or antibody to SP22, or SP22 per se, pharmaceutically acceptable carriers comprising excipients and auxiliaries which facilitate processing of the active ingredients into preparations for pharmaceutical use can be included. Preferably, the preparations contain from about 0.1 to about 99 percent, preferably from about 25 to 85 percent, of active ingredient, together with the excipients. The excipients may be any pharmaceutically acceptable excipients or carrier which can be used with the antigen or antibody.

Suitable excipients are, in particular, fillers such as sugars, including lactose, sucrose, mannitol, and sorbitol, cellulose preparations and derivatives and/or calcium phosphates. Also useful as excipients are binders such as starch, gelatin, gums, methyl cellulose, hydroxypropylmethylcellulose, sodium carboxymethylcellulose, and/or polyvinylpyrrolidone. Lubricants such as silica, talc, stearic acid, or salts thereof, and/or polyethylene glycol can also be used.

For vaginal application, suppositories, lotions, creams, sprays, or foams may be used to incorporate the active ingredients. Suitable suppository bases are, for example, natural or synthetic triglycerides, paraffin hydrocarbons, polyethylene glycols or higher alkanols. Foam formulations may include oily suspensions or aqueous solutions of the active ingredient with suitable foaming agents. Other topical carriers for vaginal applications include pharmaceutically acceptable liquids in which the active ingredient is suspended or dissolved.

For administration by nasal spray, the active ingredient is incorporated into a pharmaceutically acceptable liquid that can be sprayed into the nose.

SP22 can also be used to identify male animals who are good candidates for supplying sperm for artificial insemination. Since many livestock animals are reproduced by artificial insemination or embryo transfer, it is important to be able to identify males who are fertile as well as possessing desirable characteristics to pass on to the next generation. Techniques for reproducing animals by embryo transfer are described in U.S. Pat. Nos. 3,854,479; 4,816,257; and 4,326,505, the entire contents of each of which are hereby incorporated by reference. By determining the amount of SP22 in the sperm of a subject animal, the fertility of the animal can be predicted.

It is known that sperm proteins are affected by toxicants and pollutants. According to the present invention, the changes in SP22 level are calibrated to predict the likelihood of the sperm having been rendered infertile because of exposure to the toxicant.

In Klinefelter et al., 1996, it was demonsrated that endocrine-disruptive chemicals decreased the fertilizing ability of cauda epidiymal sperm if four days. Tests were conducted to determine if this infertility was related to decrease of SP22 associated with the sperm.

In order to evaluate the effects of exposure to toxicants that perturb the androgen status of the animal, such as EDS, sperm are subjected to analysis of SP22. Adult (90 to 120 day old) male Sprague-Dawley rats were housed two to three per cage with laboratory-grade pine shavings as bedding. The rats were maintained under controlled temperature (22° C.) and humidity (40–50%) conditions, and were given Purina laboratory rat chow and tap water ad libitum. Males were maintained in a 14-hour light, 10-hour dark schedule. Each male was numbered and randomly assigned to a treatment group. The test toxicant was administered either as a single intraperitoneal injection or as four daily injections. After four days the rats were killed, and the caudal epididymides of each rat was placed in a 35-mm culture dish containing 2 mL of Medium 199. Detergent extracts representing $10-40\times10^6$ sperm, depending on treatment, were prepared and aliquots equivalent to 30 micrograms were electrophoresed in a mini, two dimensional electrophoresis system (BioRad) for quantitative analysis of SP22. Specifically, sperm were transferred to a microcentrifuge tube and washed twice by centrifugation (300×g, five minutes) in Dulbecco's phosphate buffered saline, pH 7.2, with freshly added 0.2 extracted phenylmethylsulfonyl fluoride (PMSF). After the final wash, the sperm were extracted for one hour at room temperature with 1 mL of 40 extracted n-octyl-β-glucopyranoside in 10 ml extracted Tris, pH 7.2, containing freshly added PMSF. Following a final centrifugation at 3000×g, the supternatant was removed and frozen at −70° C.

Upon thawing, each extract was concentrated in 1 extracted Tris buffer by two centrifugations (3000×g for 45 minutes at 4° C.) in Centricon-10 units (Amincon). Protein concentration was determined using a Pierce protein assay kit. Sample volumes containing 30 $\mu$g protein were lyophilized, and protein was solubilized for 30 minutes at room temperature in 45 $\mu$L of sample buffer consisting of 5.7 g urea, 4 mL 10% NP-40, 0.5 mL ampholytes (70% 3–10, 30% 5–7) and 0.1 g dithiothreitol per 10 mL. Isoelectic focusing (750 V, 3.5 hours) was conducted in gels consisting of 6.24 g. urea, 1.5 g acrylamide (30% acrylamide, 1.2% bisacrylamide), 2.25 mL 10% NO-40, and 0.65 mL ampholytes (60% 3–10, 40% 5–7) per 10 mL. Molecular weight separation was conducted in 11% methanol and silver stained. A Kepler two dimensional gel analysis system (Large Scale Biology Corp., Rockville, Md.) was used for background correction, spot matching, and spot area quantitation. Images were acquired by transmitters at 80 $\mu$m spatial resolution and 4096 gray levels on an Ektron 1412 scanner and converted to 256 gray levels. Quantitation was done by fitting two-dimensional Gaussian distributions to the density distribution of the spot area following background subtraction. Of the 124 proteins (spots) that were identified in the 50 gel data set, 22 were common to gels representative of sperm extracts of vehicle-treated animals. Of these 22 proteins, only SP22 was affected by all test chemicals in a dose-related fashion. In fact, SP22 was the only one of the 124 that were identified, that changed in either a dose or treatment-related fashion.

It has been determined that insemination (in utero) of $5\times10^6$ epididymal sperm from a control rat results in approximately 75% fertility, thereby providing relatively greater sensitivity than insemination of a number of sperm that would result in 100% fertility.

The various data (fertility and SP22, as well as other endpoints such as motility parameters and testosterone concentrations) were collected and analyzed using two-way analysis of variance for both black and treatment effects. An initial analysis was performed to determine whether experimental block differences influenced the parameters measured. Where overall block effects are significant ($p<0.05$), the least-square means were compared for significant ($p<0.05$) treatment differences. A correlation analysis was performed to determine whether significant ($p<0.01$) correlations exist between each of the measured endpoints, and fertilizing ability and Pearson correlation coefficients (R) were calculated.

In a study reported in Klinfelter et al., *Journal of Andrology* 14(4):318–327, 1994, the authors used in utero insemination of epididymal sperm and exposure to a chemical which disrupts androgen status of the epididymis, ethane dimethanesulfonate, EDS, to investigate the hypothesis that EDS compromises the fertilizing ability of sperm by affecting epididymal function directly. Fertilizing ability, sperm motility, serum testosterone, and tissue testosterone were evaluated. In addition, sperm proteins were extracted and analyzed by quantitative two dimensional gel electrophoresis. An 18 kD protein was well correlated with fertility. However, it was felt that changes in this protein were not sufficient either to EDS itself of the dose that was tested.

In a subsequent study, the insemination procedure was modified to permit assessment of fertility (implants/corpora lutea) rather than fertilizing ability (percentage of eggs fertilized). In this study, multiple chemicals that disrupt endocrine status were tested. Adult males were exposed either to 25 or 50 mg/kg EDS, epichlorohydrin, 3 or 6 mg/kg, or hydroflutamide, 12.5 or 25.0 mg/kg, or chloroethylmethanesulfonate, 12.5 or 18.75 mg/kg. Each of these compounds perturbs the endocrine balance of the male reproductive system. The animals exposed to the known antiandrogen hydroglutamate were castrated and implanted with testosterone implants just prior to the first injection. The vehicle controls for all treatments except hydroxyflutamide received daily injections of 30% DMSO in water. The vehicle controls for the hydroxyflutamide animals were castrated, implanted with testosterone implants, and given daily injection of 15% ethanol. Four days after the onset of dosing, the males were killed and the epididymides were removed. The caput-corpus was frozen on dry ice for subsequent steroid extraction and testosterone assay. Sperm were released from the epididymal tubule into insemination medium and held in $CO_2$ incubator at 34° C. for no more than 15 minutes until insemination. Adult, estrus-synchronized female rats were monitored for lordosis behavior just after lights out on the day of insemination. Females displaying mating behavior were cervically stimulated with vasectomized teaser males at least 15 minutes prior to insemination. A volume equal to $5 \times 10^6$ sperm was inseminated into each uterine horn at day 0. On day 9, the females were killed and fertility was assessed. A Kepler two dimensional gel analysis system (Large Scale Biology Corp., Rockville, Md.) was used for background correlations, spot matching, and spot area quantitation. Images were acquired by transmittance at 80 $\mu$m spatial resolution and 4096 gray levels. Quantitation was done by fitting two-dimensional Gaussian distributions to the density distribution of the spot area following background subtraction. Of the 125 proteins (spots) that were identified in the 50 gel data set, 22 were common to gels representative of sperm extracts of vehicle-treated animals. Of these 22 proteins, only SP22 was affected by all test chemicals in a dose-related fashion. In fact, SP22 was the only one, of the 124 that were identified, that changed in either a dose or treatment-related fashion.

Measurements of sperm motion and sperm morphology were not significantly affected by any of the treatments. Based on scatter plot of the data relating the amount of SP22 to fertility (frequent), fertility classes greater and less than n 50% were chosen. Variables were then entered into the discriminant analyst to predict fertility by class, as shown in Table 1. Since, in this study, fertility for the control animals was targeted at 68%±a standard deviation of 18%; 50% represented a reasonable cutoff for the fertile class.

TABLE 1

Discrimination Analysis Based on SP22

| CLASS | PERCENTAGE CORRECTLY PREDICTED |
| --- | --- |
| Fertile (>50%) | 90 (17/19) |
| Subfertile (<50%) | 94 (29/31) |

A regression analysis showed that the amount of SP22 was significantly correlated to fertility ($p<0.0001$; $r^2$-0.83) A nonlinear fit of the data was indicated, since a threshold of 10,000 integrated optical density units of SP22 was necessary to achieve greater than 50% fertility.

Thus, by entering the level of SP22 of a sperm sample into an appropriate mathematical model, it is possible to predict the fertility of the sperm sample with a reasonably high degree (i.e., >90%) of success. An antibody to SP22 can be used to evaluate the fertility of sperm in an epididymal sperm sample or an ejaculate. Since the antibody to SP22 recognizes a single protein on immnoglots of cells of both human and stallion sperm extracts, this antibody will most likely be applicable to evaluation of animals in which maximum fertility is important, e.g., cattle, horses, dogs, and humans among other animals.

The toxicants tested above do perturb the endocrine balance of the male reproductive system. Other environmentally relevant endocrine disruptors, such as dioxin, could also compromise the expression of SP22. The present invention thus includes a screening kit to test such chemicals.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

REFERENCES

Amann, et al. Responses of Mammalian Sperm Exposed to Synthetic FertPlus™Peptide. J. Androl. Suppl.: 102A (1998a).

Amann, et al. Exposure of Human, Bull, or Boar Sperm to a Synthetic Peptide Increases Binding to an Egg-Membrane Substrate. J. Andro. (Submitted, 1998b).

Benton, et al. Screening λgt Recombinant Clones by Hybridization to Single Plaques in situ. Science, 196:180 (1997).

Burks, et al. Interaction of a Tyrosine Knase from Human Sperm with the Zona Pellucida at Fertilization. Science, 269:83–89 (1995).

Cohen, et al. Mammalian Sperm-Egg Fusion: The Development of Rat Oolemma Fusibility during Oogenesis Involves the Appearance of Binding Sites for Sperm Protein "DE". Biol. Reprod. 55:200–206 (1996).

Capkova, et al. Binding of Boar Spermatozoa to Porcine Oocytes: Effect of Low Molecular Weight 170 kDa Protein. Mol. Reprod. Devel. 46:168–175 (1997).

Causnicu, et al. Antibodies Against Epidydimal Glycoproteins Block Fertilizing Ability in Rat. J. Reprod. Fert. 72:467–471 (1984).

Gerena, et al. Identification of a Fertility-Associated Protein in Bull Seminal Plasma as Lipocalin-Type Prostaglandin D Synthase. Boil. Reprod. 58:826–833 (1998).

Hammerstedt, et al. A Method and Use of Polypeptide in Sperm-Egg Binding to Enhance or Decrease Fertility. International Patent Publication #WO/97/25620 (1997).

Hunnicutt, et al. Sperm Surface Protein PH-20 is Bifunctional: One Activity is a Hyaluronidase and a Second, District Activity is Required in Secondary Sperm-Zona Binding. Biol. Reprod. 55:80–86 (1996).

Killian, et al. Fertility-Associated Proteins in Holstein Bull Seminal Plasma. Biol. Reprod. 49:1202–1207 (1993).

Killian, et al. Alteration and Prediction of Male Fertility using Seminal Plasma and its Components. U.S. Pat. No. 5,569,581 (1996).

Klinefelter, et al. Discriminant Analysis Indicates a Single Sperm Protein (SP22) is Predictive of Fertility Following Toxicant Exposure. J. Andrology, 18:139–150 (1997).

Klinefelter, et al. Reduced Fertility is Correlated with SP22 Levels Following Exposure to the Disinfection Byproduct of Drinking Water, Bromochloroacetic Acid. J. Androl. (Manuscript in Prep.)

Lea, et al. Cloning and Sequencing of cDNAs Encoding the Human Sperm Protein, Sp17. Biochimica. Bioshysica Acta, 1307:263–266 (1996).

Linder, et al. Dibromoacetic Acid Affects Reproductive Competence and Sperm quality in the Male Rat. Fund. Appl. Toxicol. 289:9–17 (1995).

Linder, et al. Histopathologic Changes in the Tests of Rats Exposed to Dibromoacetic Acid. Reprod. Toxicol. 11:47–56 (1997).

Linder, et al. Spermatoxicity of Dichloroacetic Acid. Reprod. Arch. Androl. 32:681–688 (1994).

Wei., et al. Fertility Studies with Antisperm Antibodies. Arch. Androl. 32:251–262 (1994).

Nagakubo, et al. A Novel Oncogene Which Transforms Mouse NIH3T3 Cells in Cooperation with Ras. Biochem. Biophs. Res. Comm. 231:509–513 (1997).

O'Rand, et al. Monoclonal Antibodies to Rabbit Sperm Autoantigens. I. Inhibition of In Vitro Fertilization and Localization on the Egg. Biol. Reprod. 30:721–730 (1984).

O'Rand, et al. Sperm Antigen Corresponding to a Sperm Zona Binding Protein Autoantigenic Eptitope. U.S. Pat. No. 5,480,799 (1996).

Primakoff, et al. Reversible Contraceptive Effect of PH-20 Immunization in Male Guinea Pigs. Biol. Reprod. 56:1142–1146 (1997).

Peknicova, et al. Binding of Boar Spermatozoa to Porcine Oocytes: Effect of Low Molecular Weight 17-kDa Protein. Mol. Reprod. Devel. 46:168–175 (1997).

Sanger, et al. DNA Sequencing with Chain Terminating Inhibitors. Proc. Natl. Acad. Sci. USA 74:5463–5467 (1977).

Welch, et al. Expression of a Blyceraldehyde 3-phosphate Dehydrogenase Gene Specific to Mouse Spermatogenic Cells. Biol. Reprod. 46:869–878 (1992).

Welch, J. E Barbee, R. R., Roberts, N. L, Suarez, J. D., and Klinefelter, G. R., SP22: a Novel Fertility Protein from a Highly Conserved Gene Family. J. Andrology 19:395–398 (1998)

Klinefelter, G. R. and Welch, J. E., The Saga of a Male Fertility Protein (Sp22). Annual Review of Biomedical Sciences 1:145–184 (1999).

Eidne, K. A., Henery, C. C., and Aitken, R. J. Selection of Peptides Targeting the Human Sperm Surface using Random Peptide Phage Display to Identify Ligands Homologous to ZP. Biol. Reprod. 63:1396–1402 (2000).

O'Rand, M G and Widgren, E E, Identification of Sperm Antigen Targets for Immunocontraception; B-Cell Epitope Analysis for SP17. Reprod. Fertil. Dev. 6: 189–196 (1994).

What is claimed is:

1. A purified antibody that binds a peptide sequence of SP22 (SEQ ID NO: 3) exposed on the sperm surface.

2. The purified antibody of claim 1, which binds to a peptide sequence which is contained within the peptides sequence shown as amino acids 34–48 of SEQ ID NO: 3.

3. The purified antibody of claim 1, which binds to a peptide sequence which is contained within the peptides sequence shown as amino acids 88–102 of SEQ ID NO: 3.

4. The purified antibody of claim 1, which binds to a peptide sequence which is contained within the peptides sequence shown as amino acids 118–132 of SEQ ID NO: 3.

5. The purified antibody of claim 1, which binds to a peptide sequence which is contained within the peptides sequence shown as amino acids 136–150 of SEQ ID NO: 3.

* * * * *